(12) United States Patent
Yamagata et al.

(10) Patent No.: US 8,102,392 B2
(45) Date of Patent: Jan. 24, 2012

(54) IMAGE PROCESSING/DISPLAYING APPARATUS HAVING FREE MOVING CONTROL UNIT AND LIMITED MOVING CONTROL UNIT AND METHOD OF CONTROLLING THE SAME

(75) Inventors: Hitoshi Yamagata, Otawara (JP);
Yoshitaka Mine, Nasu-gun (JP);
Naohisa Kamiyama, Otawara (JP);
Susumu Hiki, Otawara (JP); Yuko Tanaka, Shioya-gun (JP); Masaaki Tanaka, legal representative, Shioya-gun (JP); Tadashi Shiotani, legal representative, Matsue (JP); Yuriko Shiotani, legal representative, Matsue (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 10/876,662

(22) Filed: Jun. 28, 2004

(65) Prior Publication Data

US 2005/0033160 A1 Feb. 10, 2005

(30) Foreign Application Priority Data

Jun. 27, 2003 (JP) ................. 2003-184132
Nov. 20, 2003 (JP) ................. 2003-390657

(51) Int. Cl.
*G06T 17/00* (2006.01)
(52) U.S. Cl. ..................................... 345/420
(58) Field of Classification Search .................. None
See application file for complete search history.

(56) References Cited

U.S. PATENT DOCUMENTS 6,055,449 A * 4/2000 Navab ........................... 600/427
6,095,978 A * 8/2000 Takeuchi ....................... 600/443
6,801,643 B2 * 10/2004 Pieper ........................... 382/128

FOREIGN PATENT DOCUMENTS

| JP | 3-188837 | 8/1991 |
| JP | 06-337920 | 12/1994 |
| JP | 7-8497 | 1/1995 |
| JP | 9-24034 | 1/1997 |
| JP | 9-24035 | 1/1997 |
| JP | 11-155881 | 6/1999 |
| JP | 2002-112998 | 4/2002 |

OTHER PUBLICATIONS

Gering, D., A System for Surgical Planning and Guidance using Image Fusion and Interventional MR, Dec. 1999, Masters thesis, Massachusetts Institute of Technology, pp. 1-106.*
U.S. Appl. No. 11/969,387, filed Jan. 4, 2008, Yamagata.
Office Action issued Sep. 14, 2010, in Japan Patent Application No. 2004-181380.

* cited by examiner

*Primary Examiner* — Said Broome
(74) *Attorney, Agent, or Firm* — Oblon, Spivak, McClelland, Maier & Neustadt, L.L.P.

(57) ABSTRACT

An image processing/displaying apparatus comprises a data storage unit configured to store 3-dimensional volume data, a cross section information generation unit configured to generate cross section information by reconstructing the 3-dimensional volume data stored in the data storage unit, an image display unit configured to display a cross section image of a subject in accordance with the cross section information generated by the cross section information generation unit, a locking unit configured to designate an affected part in the cross section image as a rotation center and a control unit configured to control image rotation on the image display unit so that the affected part is contained in the cross section image, when operation for rotating cross section is performed by an operator.

18 Claims, 26 Drawing Sheets

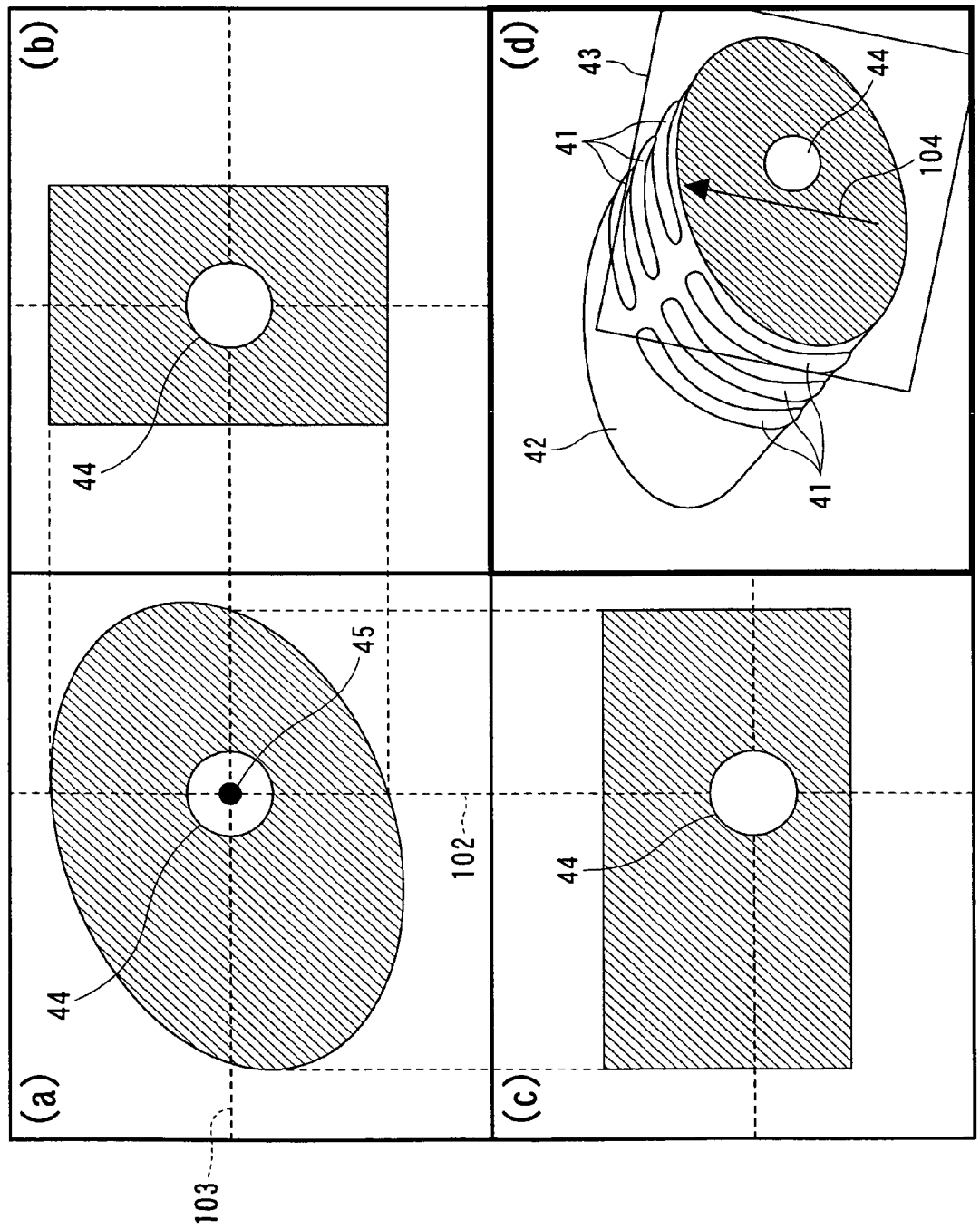

IMAGE PROCESSING/DISPLAYING APPARATUS HAVING FREE MOVING CONTROL UNIT AND LIMITED MOVING CONTROL UNIT AND METHOD OF CONTROLLING THE SAME

BACKGROUND OF THE INVENTION

1. Field of the Invention

The present invention relates to an image processing/displaying apparatus for medical use, and more particularly, to an image processing/displaying apparatus for assisting planning of paracentesis and assisting actual paracentesis in which a paracentesis needle is inserted into a subject to remove a tissue of an affected part or treat the affected part. The present invention also relates to a method of controlling such an image processing/displaying apparatus.

2. Description of the Related Art

Cancer is one of three major diseases in Japan. Of those three major diseases, only cancer is increasing in mortality. Of all types of cancer, 10% is cancer of liver and the percentage thereof is increasing. Early detection of cancer of liver has become possible as a result of advance in medical modality technology, in particular, 3-dimensional imaging technology using an ultrasonic diagnostic apparatus, an MRI scanner, or an X-ray CT scanner.

In particular, very high diagnostic ability compared with that achieved by the conventional 2-dimensional imaging technology has been achieved as a result of advances in 3-dimensional imaging technology using a CT scanner including a multiline (4-line, 8-line, 16-line, or the like) detector and having a high-speed helical scan capability and 3-dimensional imaging technology using an MRI scanner having improved performance, in particular, in terms of gradient magnetic field, high-frequency magnetic field, and RF coil, which makes it possible to take an MRI image in a short time during which breathing is stopped. In particular, great advances have been made in diagnosis using 3-dimensional CT angiography (3D-CTA).

Many therapies for cancer of liver are known. Examples are transcatheter arterial injection, transcatheter arterial embolization, minimum invasive therapy, and abdominal surgery. Of those therapies, the minimum invasive therapy is most widely used because of its advantage of low invasion to a subject.

Specific examples of minimum invasive therapies include percutaneous ethanol injection technique (PEIT) and microwave ablation. In a minimum invasive therapy, a paracentesis needle is inserted while monitoring an image of the paracentesis needle in real time using an ultrasonic diagnostic apparatus.

Of various ablation therapies, radio frequency ablation (RFA) is in the limelight and is under clinical evaluation. Specific examples of RFA include cool tip RFA using a single needle and radiofrequency interstitial tissue ablation (RITA) using a plurality of needles. In many cases, paracentesis is performed percutaneously. In some cases, treatment is laparoscopically performed using the same paracentesis fixture as described above while observing the surface of liver or while observing the inside of liver using a special ultrasonic probe in contact with the surface of liver.

However, 3-dimensional imaging tools are not widely used in planning or treatment of paracentesis or in aftercare. In recent years, it has become very popular to use a 3-dimensional imaging tool realized on a standalone workstation in medical diagnosis or treatment. However, as a tool of assisting paracentesis treatment or removal of a tissue (for a biopsy), the manner of displaying 3-dimensional images is not good enough, and a good enough user interface is not available.

Ultrasonic imaging does not allow simultaneous observation of the whole of liver and adjacent parts such as a diaphragm. Thus, there is a need for a 3D-CTA tool that makes it possible to easily find a proper needle insertion point in a highly reliable fashion. Furthermore, when a paracentesis needle insertion point is determined before paracentesis treatment is actually performed while observing an affected part using an ultrasonic imaging apparatus, it is desired to display an easy-to-understand 3-dimensional image of a 3D-CTA cross section including information associated with an ultrasonic cross section including a paracentesis needle predicted to appear in the actual paracentesis treatment. There is also a need to display a determined needle insertion point relative to a body surface and bones.

In many cases, a medical treatment room does not have a space to install a workstation or the like in addition to an ultrasonic diagnostic apparatus. This makes it impractical to use an X-ray CT scanner or the like to determine a needle insertion point in a 3-dimensional image at a time immediately before starting treatment. Thus, there is a need for an ultrasonic imaging apparatus having the capability of displaying a needle insertion point when starting paracentesis.

In view of the above, an apparatus for assisting paracentesis has been proposed which generates, from 3-dimensional volume data, a cross section image depending on the position and the angle of an ultrasonic probe used in paracentesis and displays the resultant cross section image (Japanese Unexamined Patent Application Publication No. 2002-112998). However, it is still difficult to correctly determine whether there is an obstacle on or close to a path along which to insert a needle.

Even when a needle insertion position has been determined, the determined needle insertion position on the body surface is not displayed in an easy-to-recognize manner.

There have been proposed various techniques of displaying a virtual ultrasonic cross section image superimposed on a 3D-CTA image. However, there is still a problem that a part to be treated is displayed only on an X-ray CT image and not displayed on an ultrasonic diagnostic apparatus. Even when an ultrasonic diagnostic apparatus is capable of displaying an image of a part to be treated, the image is not clear enough. Another still existing problem is that when there are two or more parts to be treated, it is difficult to perform treatment based on only images obtained in planning of treatment.

In addition, there is another problem that it is difficult to make comparison after treatment among images acquired by different kinds of modality with each other.

SUMMARY OF THE INVENTION

In view of the above, it is an object of the present invention to provide an image processing/displaying apparatus and a method of controlling the same, capable of easily and correctly determining whether there is an obstacle on or close to a paracentesis needle insertion path from an needle insertion point to an affected part to be treated.

It is another object of the present invention to provide an image processing/displaying apparatus and a method of controlling the same, capable of displaying a paracentesis needle insertion point in an easy-to-recognize manner.

It is another object of the present invention to provide an image processing/displaying apparatus and a method of controlling the same, capable of easily and correctly identifying even a tumor or tumors that would be difficult to identify using an ultrasonic imaging apparatus, during treatment or at a time immediately before starting treatment, based on information obtained in planning of the treatment.

It is also another object of the present invention to provide an image processing/displaying apparatus and a method of controlling the same, capable of easily making comparison among images acquired by different kind modality each other before planning of paracentesis or after actual paracentesis.

To achieve the above objects, the present invention provides an image processing/displaying apparatus which comprises a data storage unit configured to store 3-dimensional volume data, a cross section information generation unit configured to generate cross section information by reconstructing the 3-dimensional volume data stored in the data storage unit, an image display unit configured to display a cross section image of a subject in accordance with the cross section information generated by the cross section information generation unit, a locking unit configured to designate an affected part in the cross section image as a rotation center and a control unit configured to control image rotation on the image display unit so that the affected part is contained in the cross section image, when operation for rotating cross section is performed by an operator.

Preferably, the image processing/displaying apparatus further comprises a needle insertion path setting unit configured to set a paracentesis needle insertion path such that when an insertion point at which to insert a paracentesis needle is specified on a plane cut taken in the cross section image including the affected part or in the cross section image displayed together with the plane cut, a straight line is drawn between the specified insertion point and the affected part thereby setting the paracentesis needle insertion path.

In the image processing/displaying apparatus, preferably, when a paracentesis needle insertion path is set by the needle insertion path setting unit, the image display unit displays images of two orthogonal cross sections orthogonally intersecting along the paracentesis needle insertion path with each other and a cross section image perpendicular to the paracentesis needle insertion path such that the cross sections are in positions moved by predetermined distances within a predetermined range along the paracentesis needle insertion path. Alternatively, the image display unit may display the paracentesis needle insertion path and a region of a virtual paracentesis ultrasonic cross section in a superimposed fashion.

In the image processing/displaying apparatus, the image display unit may display a 3-dimensional image generated by means of volume rendering, and the needle insertion path setting unit may specify a paracentesis needle insertion point on the basis of the 3-dimensional image.

Alternatively, the image display unit may display an arbitrary cross section and an MPR image of three orthogonal cross sections, and the needle insertion path setting unit may specify a paracentesis needle insertion point on the basis of the arbitrary cross section and the MPR image of the three orthogonal cross sections.

The image display unit may display an image of a first cross section including a paracentesis needle insertion path set by the needle insertion path setting unit, an image of a second cross section including the paracentesis needle insertion path and perpendicular to the first cross section, a third cross section image perpendicular to the paracentesis needle insertion path, and a 3-dimensional image generated by means of volume rendering.

Alternatively, the image display unit may display a live image taken by an ultrasonic diagnostic apparatus in addition to a composite image of a 3-dimensional image including a paracentesis needle insertion path generated by means of volume rendering and a virtual ultrasonic cross section image.

In the image processing/displaying apparatus, preferably, the needle insertion path setting unit is capable of changing the specified insertion point of the paracentesis needle when some of the cross section images include a part that should be avoided from the paracentesis needle insertion path.

In the image processing/displaying apparatus, preferably, the data storage unit acquires 3-dimensional volume data from one or more of an X-ray 3-dimensional imaging apparatus, an X-ray CT scanner, an MRI scanner, an ultrasonic diagnostic apparatus, and a nucleus medical diagnostic apparatus.

The present invention also provides a method of controlling an image processing/displaying apparatus comprising a first step of displaying a cross section image of a subject in accordance with 3-dimensional volume data indicating information of a subject, a second step of setting a point specified on the image displayed in the first step, as an affected part, a third step of rotating the position of the cross section about the affected part set in the second step, generating an image of the rotated cross section on the basis of the 3-dimensional volume data, and displaying the generated image and a fourth step of specifying a point on the image displayed in the third step thereby setting a paracentesis start point.

The present invention also provides a method of controlling an image processing/displaying apparatus comprising a first step of setting a plurality of paracentesis needle insertion paths by specifying a plurality of points on an image of a cross section generated from 3-dimensional volume data indicating information of a subject, and a second step of generating cross section images in which the respective paracentesis needle insertion paths set in the first step lie, and displaying the resultant images.

The image processing/displaying apparatus may further comprise body surface image generation unit configured to generate a body surface image of the subject by means of surface rendering from the 3-dimensional volume data stored in the data storage unit, and the image display unit may display the body surface image generated by the body surface image generation unit so as to be superimposed on the 0.3-dimensional image.

Alternatively, the image processing/displaying apparatus may further comprise graphic data generation unit configured to generate graphic data indicating the position of a virtual ultrasonic cross section and graphic data indicating a paracentesis needle from the 3-dimensional volume data stored in the data storage unit, and the image display unit may display a graphic image based on the graphic data generated by the graphic data generation unit so as to be superimposed on the 3-dimensional image.

In the image processing/displaying apparatus, preferably, the image display unit displays the graphic image superimposed on the 3-dimensional image such that the graphic image is erasable.

In the image processing/displaying apparatus, the image display unit may display a mark on a surface of the subject so as to be superimposed on the 3-dimensional image.

In the image processing/displaying apparatus, the image display unit may display a center line of the subject so as to be superimposed on the 3-dimensional image.

The present invention also provides an image processing/displaying apparatus comprising a region specifying unit for specifying a region and a 3-dimensional position indicating the substantially central point of each of one or more affected parts to be treated or removed on the basis of 3-dimensional volume data associated with a 3-dimensional region including the one or more affected parts in a subject, an image display unit for displaying a 3-dimensional image including a position and a region specified by the region specifying unit, an ultrasonic probe for transmitting and receiving an ultrasonic wave to and from a part to be imaged, and a position sensor disposed on the ultrasonic probe for perceiving a relative position of the ultrasonic probe on the subject's surface, wherein the specified position of the affected part is displayed on an ultrasonic image on the basis of position information indicating the specified position of the affected part and also on the basis of data provided by the position sensor.

Preferably, the ultrasonic probe is one of a one-dimensional array ultrasonic probe, a two-dimensional array ultrasonic probe, and a mechanical probe that mechanically scans a one-dimensional array.

In the image processing/displaying apparatus, a 3-dimensionally-scanned volume shape may be displayed on the basis of the position of the region of the affected part to be treated and the position of a one-dimensional array ultrasonic probe on the subject's surface, so as to be superimposed on a 3-dimensional image including the specified position and region of the affected part. Alternatively, the shape of a volume 3-dimensionally scanned by a 2-dimensional array probe or a mechanical probe may be displayed so as to be superimposed on a 3-dimensional image including the specified position and region.

More preferably, the image display unit displays a body mark representing a shape of the subject and a probe mark indicating, on the body mark, a position at which the ultrasonic probe is in contact with the surface of the subject in accordance with information provided by the position sensor.

It is also preferable that the image processing/displaying apparatus further comprising comprises a probe graphic storage unit configured to store graphical image indicating the ultrasonic probe and a body surface image generation unit configured to generate body surface image of the subject by means of surface rendering from the 3-dimensional volume data; and the image display unit displays the graphical image if of the ultrasonic probe so as to superimposed on the body surface image generated by the body surface image generation unit in a position of the ultrasonic probe calculated from the data obtained by the position sensor.

The present invention also provides a method of controlling an image processing/displaying apparatus comprising a first step of displaying a cross section image extracted from 3-dimensional volume data including an affected part specified before starting treatment and also displaying a real-time 2-dimensional cross section image, and a second step of, after the real-time 2-dimensional cross section image and the cross section image become substantially identical to each other, simultaneously and synchronously displaying the real-time 2-dimensional cross section image and the cross section image under the assumption that the space coordinates of the 3-dimensional volume data and the imaging space coordinates based on information provided by the position sensor installed on the ultrasonic probe.

It is also preferable that the image processing/displaying apparatus according to claim 13, further comprises a probe graphic storage unit configured to store a graphical image representing a paracentesis probe and physical relationship between the paracentesis probe and a paracentesis needle, wherein the image display unit displays the graphical image representing a paracentesis probe at the location where the paracentesis probe touches body surface of the body surface image and where plane cut intersects the body surface so as to be superimposed on the body surface image generated by the body surface image generating unit.

According to the present invention, as described above, an image processing/displaying apparatus can be achieved which is capable of easily and correctly determining whether there is an obstacle on or close to a paracentesis needle insertion path from an needle insertion point to an affected part to be treated.

Furthermore, the image processing/displaying apparatus according to the present invention is capable of displaying a paracentesis needle insertion point in an easily recognizable manner.

The image processing/displaying apparatus according to the present invention is also capable of easily and correctly identifying even a tumor or tumors that would be difficult to identify using an ultrasonic imaging apparatus, during treatment or at a time immediately before starting treatment, based on information obtained in planning of the treatment.

In addition, the image processing/displaying apparatus according to the present invention is capable of easily making comparison among images acquired by different kind modality each other before planning of paracentesis or after actual paracentesis.

BRIEF DESCRIPTION OF THE DRAWINGS

FIGS. 6A to 6C are diagrams showing examples of cross section images including a paracentesis needle insertion path, wherein FIG. 6A shows a volume rendering image including a plane cut, FIG. 6B shows an image of a virtual ultrasonic cross section including an ROI, and FIG. 6C shows three cross section images including a paracentesis needle insertion path and being perpendicular to each other;

FIG. 9 is a diagram showing an example of a manner in which a plane cut including an affected part is set using a MPR image in an image processing/displaying apparatus according to a second embodiment of the present invention;

FIGS. 13A to 13C are diagrams showing an example of a manner of setting a plane cut including an affected part using a maximum intensity projection image or a volume rendering image whose transparency is allowed to be adjusted in an image processing/displaying apparatus according to a third embodiment of the present invention, wherein FIG. 13A shows an example of an image being observed, FIG. 13B shows an example of an image in which voxel data having highest pixel intensity is embedded in original volume data, and FIG. 13C shows an example of a volume rendering image rotated from the position shown in FIG. 13B;

DESCRIPTION OF THE PREFERRED EMBODIMENTS

First Embodiment

Figure 1:
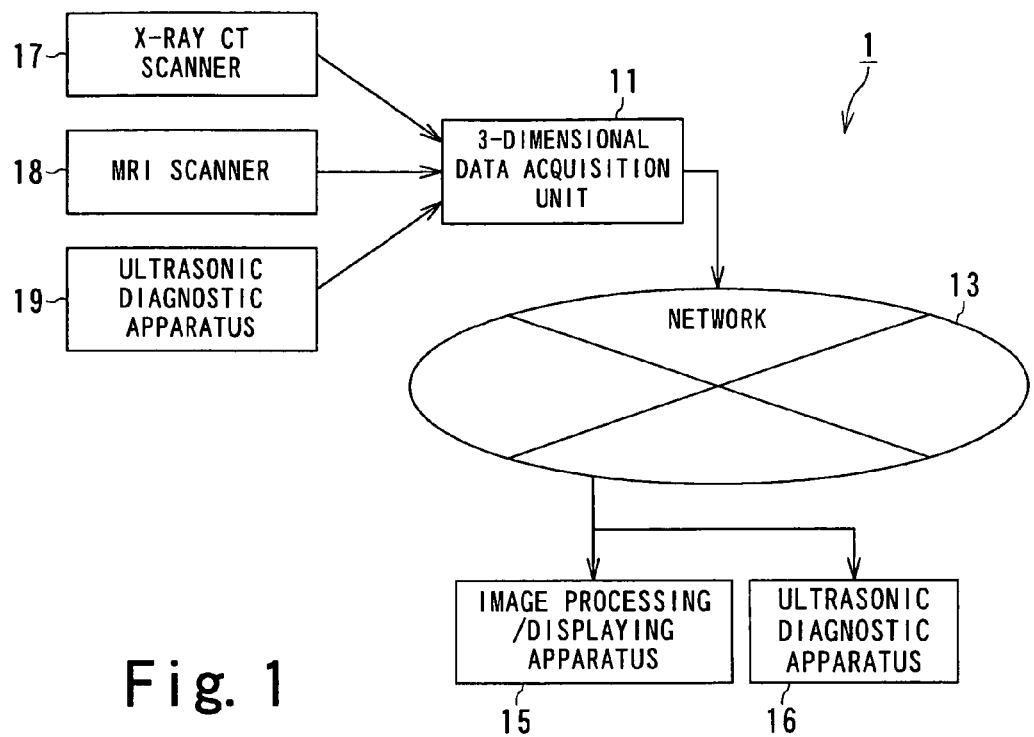
FIG. 1 is a diagram generally showing a diagnostic system including an image processing/displaying apparatus according to a first embodiment of the present invention.

An image processing/displaying apparatus according to a first embodiment of the present invention is described below with reference to the accompanying drawings. FIG. 1 is a diagram showing an overall structure of a diagnostic system 1 including an image processing/displaying apparatus for medical use according to the first embodiment of the present invention. The diagnostic system 1 includes a 3-dimensional data acquisition unit 11 for acquiring 3-dimensional data, a network 13 such as a local area network (LAN) disposed in a hospital for transmitting the 3-dimensional volume data acquired by the 3-dimensional data acquisition unit 11, a image processing/displaying apparatus 15 for receiving the 3-dimensional data transmitted via the network 13, processing the received 3-dimensional data as will be described later, and displaying the resultant 3-dimensional data, and an ultrasonic diagnostic apparatus 16 for displaying a real-time image of a paracentesis needle inserted into a patient's body.

The 3-dimensional data acquisition unit 11 is connected, directly or indirectly via a network, for example, to an X-ray computerized tomography (CT) scanner 17 for taking an X-ray CT image of a patient's body, a magnetic resonance imaging (MRI) scanner 18 for taking an MR tomographic image of a patient's body, and/or an ultrasonic diagnostic apparatus 19 for taking an ultrasonic tomographic image (hereinafter, those imaging apparatuses will be generically referred to as modality imaging apparatuses). 3-dimensional volume data output from those modality imaging apparatuses are transmitted to the 3-dimensional data acquisition unit 11 directly or indirectly via the network.

The 3-dimensional data acquisition unit 11 may include an internal unit for processing acquired data and displaying resultant data or may be connected to an external image processing/displaying apparatus realized by a workstation or the like. Alternatively, the 3-dimensional data acquisition unit 11 may be disposed in each modality imaging apparatus.

Figure 2:
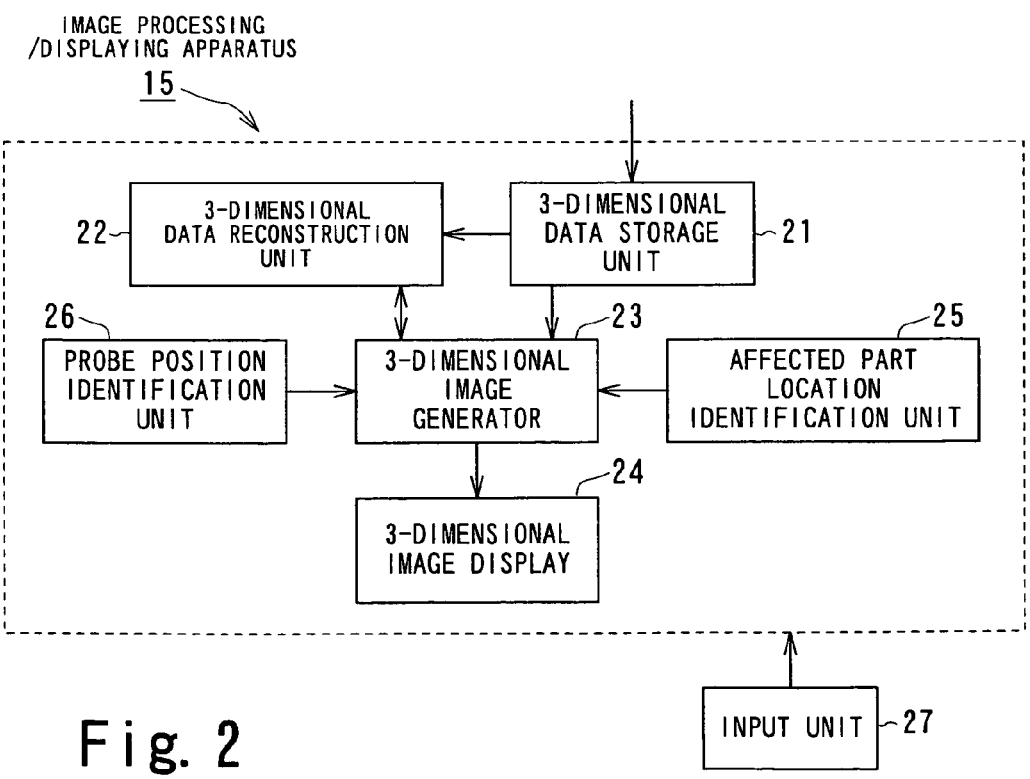
FIG. 2 is a block diagram showing a general structure of an image processing/displaying apparatus according to a first embodiment of the present invention.

As shown in FIG. 2, the image processing/displaying apparatus 15 includes a 3-dimensional data storage unit 21 for storing 3-dimensional volume data acquired via the network 13, a 3-dimensional data reconstruction unit 22 for reconstructing a 3-dimensional image by processing the 3-dimensional data stored in the storage unit 21, a 3-dimensional image generator 23 for generating 3-dimensional image including cross section image from data reconstructed by the 3-dimensional data reconstruction unit 22, a 3-dimensional image display 24 for displaying a 3-dimensional image in accordance with the data generated by the 3-dimensional image generator 23, an affected part location identification unit 25 for identifying the location of an affected part, based on the cross section image including an affected part displayed on the 3-dimensional image display 24, and supplying information indicating the identified location to the 3-dimensional image generator 23, and a probe position identification unit 26 for identifying the position of a paracentesis probe and supplying data indicating the identified position to the 3-dimensional image generator 23. The storage unit 21 includes a storage medium such as a semiconductor memory, a hard disk, a CD-ROM, a flexible disk, or a memory card.

The image processing/displaying apparatus 15 is realized, for example, by a workstation and is controlled by a CPU (not shown). Alternatively, the image processing/displaying apparatus 15 may be disposed in an integrated form in the ultrasonic diagnostic apparatus 16 such that the ultrasonic diagnostic apparatus 16 has an image processing/displaying capability.

An input unit 27 serves as an interface used by a user such as a medical doctor to input various commands to the image processing/displaying apparatus 15. As described later, a paracentesis needle insertion path is set by inputting commands via the input unit 27. In the case in which the image processing/displaying apparatus 15 is realized by a workstation, for example, a keyboard, a mouse, and/or the like are used as the input unit 27. In the case in which the image processing/displaying apparatus 15 is disposed in an integrated form in the ultrasonic diagnostic apparatus 16, for example, a control panel, a trackball, a touch command screen (TCS), and/or the like are used as the input unit 27.

When a paracentesis needle is inserted, the ultrasonic diagnostic apparatus 16 takes an image of an affected part of a subject and the paracentesis needle by using a probe and displays the image such that the locations of the affected part and the paracentesis needle are indicated. Although in the present embodiment, by way of example, paracentesis is performed using the ultrasonic diagnostic apparatus 16, paracentesis may also be performed using another type of modality imaging apparatus such as an X-ray CT scanner or an MRI scanner.

The operation of the image processing/displaying apparatus 15 constructed in the above-described manner is described below with reference to a flow chart shown in FIG. 3.

3-dimensional volume data such as CT angio image data produced by a modality imaging apparatus such as an X-ray CT scanner 17 is acquired by the 3-dimensional data acquisition unit 11 and transmitted via the network 13 to the 3-dimensional data storage unit 21 of the image processing/displaying apparatus 15 (step S301).

Instead of transmitting 3-dimensional volume data via the network, 3-dimensional volume data may be stored on a storage medium such as an MO, a CD-R, or a DVD-R and the 3-dimensional volume data may be directly input to the ultrasonic diagnostic apparatus 16 or the image processing/displaying apparatus 15 using the storage medium.

After the 3-dimensional volume data stored in the 3-dimensional storage unit 21 is reconstructed into voxel data suitable for 3-dimensional image processing by the 3-dimensional data reconstruction unit 22, the data is further reconstructed by the 3-dimensional image generator 23 into a cross section image and/or rendering image. The resultant image is displayed on the 3-dimensional image display 24 (step S302).

From the 3-dimensional volume data, data indicating three orthogonal cross sections are generated. They are an axial cross section orthogonal to a body axis, a sagittal cross section orthogonal to the front plane and the body axis plane of a patient's body, and a coronal cross section parallel to the front plane of the subject and orthogonal to the body axis plane. In an initial state, an axial cross section is selected as a plane cut 43, and a volume rendering image thereof is displayed on the 3-dimensional image display 24 as shown in FIG. 4A.

Figure 4A:
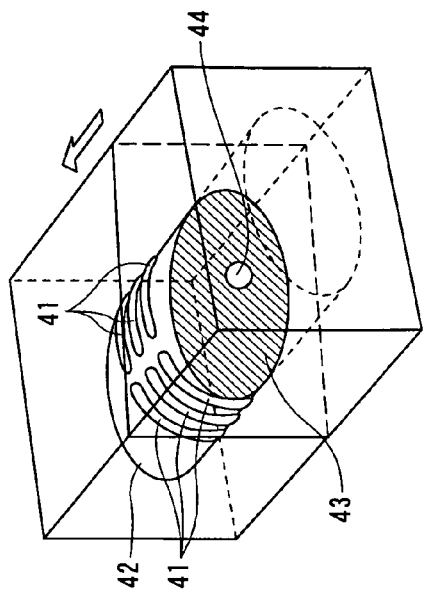
FIGS. 4A to 4D are diagrams showing examples of 3-dimensional images displayed in accordance with the first embodiment of the present invention, wherein a plane cut is set in an example shown in FIG. 4A, the plane cut is displaced in FIG. 4B, the plane cut is rotated in a clockwise direction in FIG. 4C, and the plane cut is rotated in a counterclockwise direction in FIG. 4D.

As shown in FIG. 4A, the image may be displayed such that a region 41 of bones represented by CT values and the other region 42 are simultaneously displayed by adjusting the transparency in volume rendering or such that the two regions are simultaneously displayed as separate volumes. In FIG. 4A, reference numeral 43 denotes a plane cut (PC) indicating a cross section at a temporary position.

Figure 3:
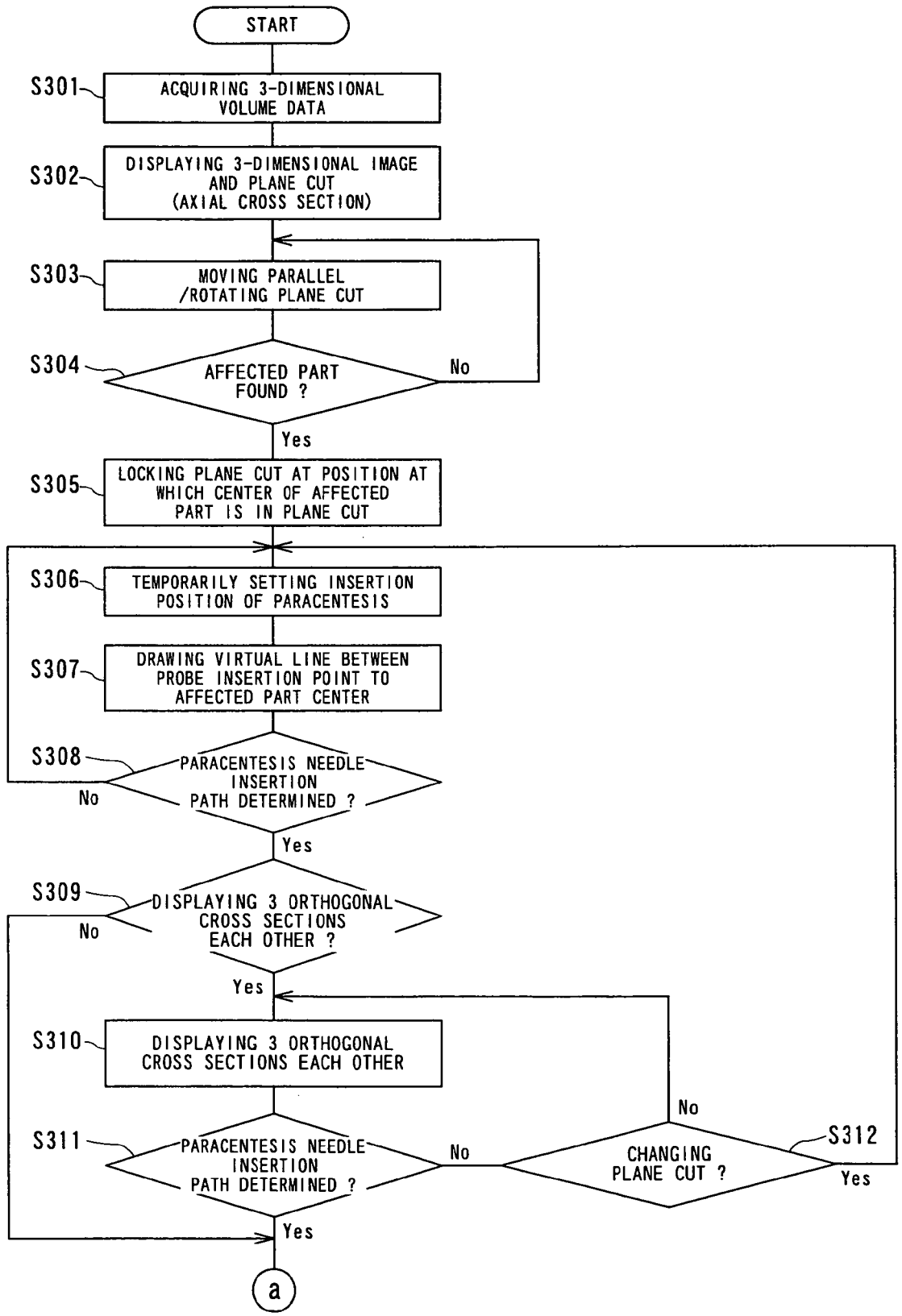
FIG. 3 is a flow chart showing an operation of the image processing/displaying apparatus according to the first embodiment of the present invention.

In step S303 shown in FIG. 3, if a user specifies an amount and a direction of movement or rotation by moving or rotating a pointing device (not shown) such as a mouse or a trackball of the input unit 27, the CPU (not shown) transmits a signal to the probe position identification unit 26 so that the cross section (plane cut) 43 of the 3-dimensional volume is moved in parallel or rotated by the specified amount in the specified direction, and the resultant image of the cross section is displayed.

Figure 4B:
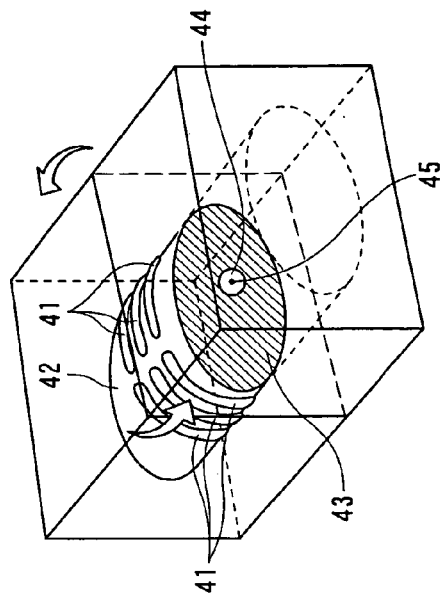
Figure 4C:
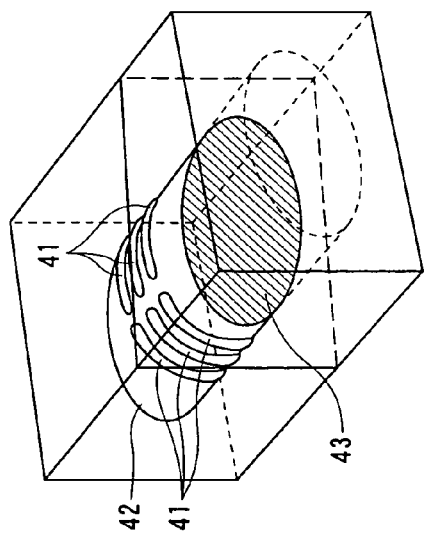
Figure 4D:
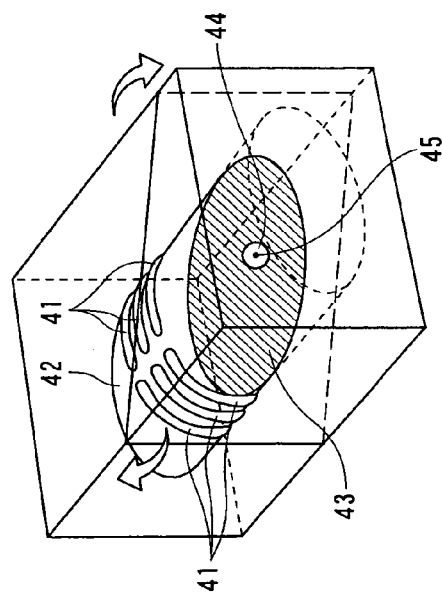

FIG. 4B shows an example in which a plane cut 43 taken in an axial cross section is moved in parallel from an initial position. FIG. 4C shows an example in which the plane cut 43 taken in the axial cross section is rotated in a clockwise direction from its initial position while maintaining the orthogonality between the axial cross section and a sagittal plane. FIG. 4D shows an example in which the plane cut 43 taken in the axial cross section is rotated in a similar manner but in a counterclockwise direction.

The user performs such a parallel displacement or rotation on the plane cut 43 until an affected part 44 to be treated is found (steps S303 and S304).

If the plane cut 43 is set such that the affected part 44 is passed through by the plane cut 43 as shown in FIG. 4B (that is, the answer to step S304 is yes), then, as shown in FIG. 4C, the user moves a cursor by operating the mouse or the like (not shown) of the input unit 27 so that the cursor points to the affected part center 45. In this state, if the user clicks the mouse, a signal is transmitted from the mouse to the CPU. In response, the CPU transmits a command to the affected part location identification unit 25 shown in FIG. 2 to identify the location of the affected part 44.

In step S305, the affected part location identification unit 25 designates an affected part in the cross section image as a rotation center and locks the plane cut 43 at a position at which the affected part center 45 is in the plane cut 43. Then the affected part location identification unit 25 controls image rotation on the image display unit so that the affected part is contained in the cross section image, when operation for rotating cross section is performed by an operator. Once the plane cut 43 is locked, parallel displacement of the plane cut 43 is disabled. If the plane cut 43 is rotated in this state, the affected part center 45 is maintained in the plane cut 43 as shown in FIG. 4D. That is, in the present embodiment of the invention, the probe position identification unit 26 also serves as locking unit and a control unit.

In step S306, an insertion position of a paracentesis probe into a body via a surface of the body is temporarily set. More specifically, the user moves the cursor displayed on the 3-dimensional image display 24 by operating the pointing device (not shown) such as a mouse or a trackball of the input unit 27 so that the cursor points to a point that is in the plane cut 43 and that is on the body surface. Thereafter, if the mouse is clicked, a signal is transmitted to the CPU (not shown). In response, the CPU transmits a command to the probe position identification unit 26 to temporarily set the insertion position.

Figure 5A:
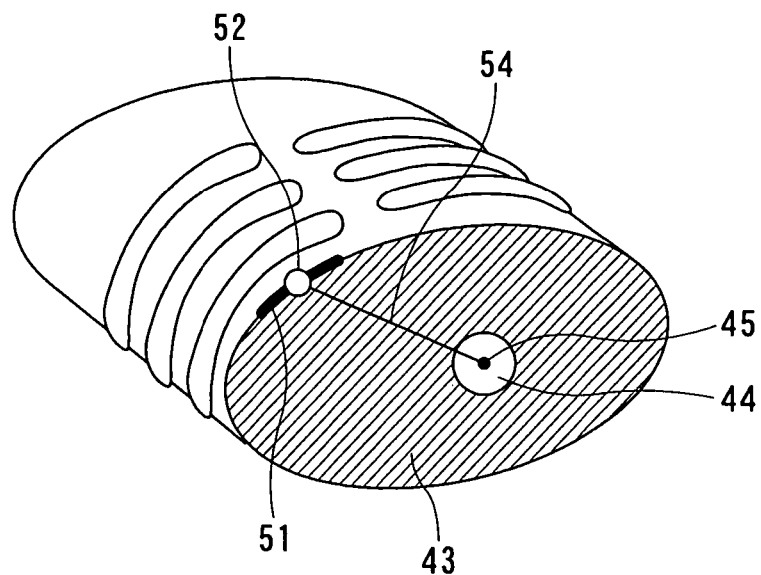
FIGS. 5A and 5B are diagrams illustrating a manner in which a paracentesis needle insertion path is set by specifying a paracentesis needle insertion point, wherein in FIG. 5A the paracentesis needle insertion point is temporarily set at the center of a line along which to put a paracentesis probe, while in FIG. 5B the paracentesis needle insertion point is temporarily set at an end the line.

More specifically, first, a line 51 on which to put the paracentesis probe is set on an edge of the plane cut 43, as shown in FIG. 5A. Setting of the line 51 is performed as follows. An image is taken using the X-ray CT scanner 17 such that spaces between costas are represented in the image. In this image, two landmarks or a line having a higher CT value and thus having a higher intensity than those of bones are specified on the edge of the plane cut 43.

Figure 5B:
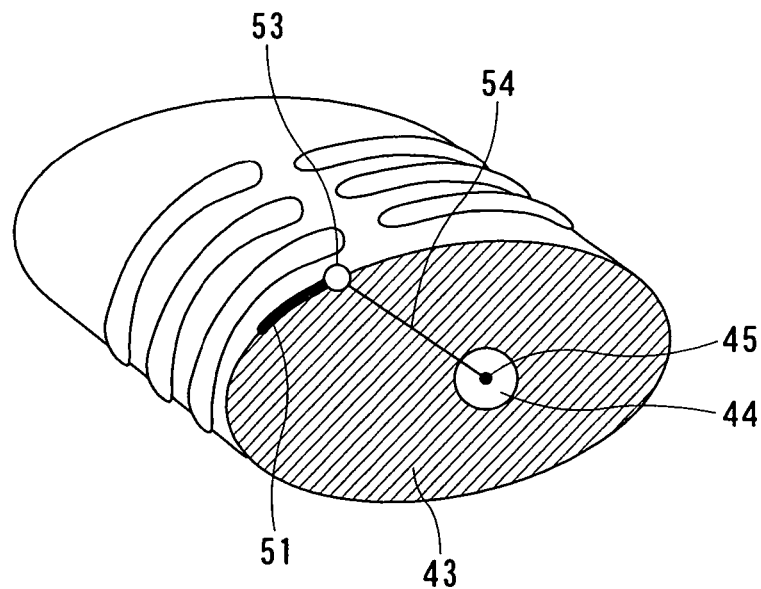

If the user specifies a point on the line 51 by clicking the mouse, the insertion point is temporarily set at that point. In the setting of the insertion point, the point may be set at the line center 52 as shown in FIG. 5A, or at an end 53 of the line 51 on which to put the paracentesis probe, as shown in FIG. 5B. Thus, in the present embodiment of the invention, the probe position identification unit 26 also serves as needle insertion path setting unit.

If the probe insertion point is temporarily set in the above-described manner, the process proceeds to step S307. In step S307, the probe position identification unit 26 draws a virtual line 54 between the probe insertion point to the affected part center 45. This line 54 indicates a temporarily set paracentesis needle insertion path to the affected part from the temporarily set probe insertion point.

At this stage, the user determines whether the temporarily set paracentesis needle insertion path 54 is sufficiently apart from any blood vessel or the like so that the insertion of the paracentesis probe will not damage any blood vessel or the like. In the case in which the paracentesis needle insertion path 54 is not sufficiently apart from some blood vessel (that is, if the distance between the paracentesis needle insertion path 54 and some blood vessel is less than, for example, 10 mm), the paracentesis needle insertion path 54 is not a proper path. Information necessary to determine whether the paracentesis needle insertion path 54 is sufficiently apart from any blood vessel or the like can be obtained by rotating the locked plane cut 43 passing through the affected part center 45.

If some blood vessel or the like is found close to the temporarily set paracentesis needle insertion path 54, the temporarily set paracentesis needle insertion path 54 is cancelled (that is, the answer to step S308 becomes no) and the process returns to step 306 to temporarily set the paracentesis needle insertion point at a different point. The above-described process is performed repeatedly until the paracentesis needle insertion path 54 is finally determined.

If the temporarily set paracentesis needle insertion path 54 is sufficiently apart from any blood vessel or any similar part that should be avoided, the user moves the cursor to an "insertion path determination" button displayed on the screen of the 3-dimensional image display 24 by operating the mouse or the like and clicks the button thereby transmitting a command to the CPU of the image processing/displaying apparatus 15 to employ the current paracentesis needle insertion path 54 as a finally determined paracentesis needle insertion path 54. In response to receiving the command, the CPU transmits a signal to the probe position identification unit 26 to employ the current paracentesis needle insertion path 54 as a finally determined paracentesis needle insertion path 54 (the answer to step S308 becomes yes).

As described above, temporary setting of the paracentesis needle insertion path 54 along a straight line between the affected part center and the paracentesis needle insertion point makes it possible to easily determine whether the paracentesis needle insertion path 54 is sufficiently apart from any part that should be avoided. That is, it becomes possible to quickly and easily determine a proper paracentesis needle insertion point even at a time immediately before starting paracentesis.

Figure 6A:
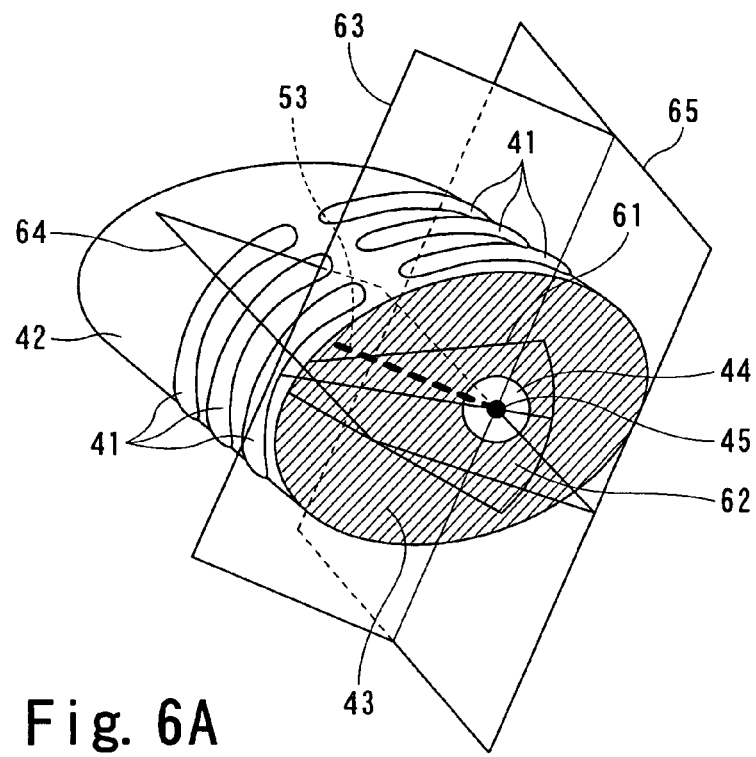

In order to determine the paracentesis needle insertion point in a still more reliable fashion, additional steps described below may be performed. That is, in step S309, in accordance with a command issued by the user, the CPU commands the 3-dimensional image generator 23 to generate images of a total of three cross sections, that is, two orthogonal cross sections 63 and 64 intersecting each other along the temporarily set paracentesis needle insertion path (straight line) 54 and a cross section 65 orthogonal to the line of intersection of the two cross sections 63 and 64, as shown in FIG. 6A. The user is prompted to determine whether those three cross sections are displayed on the 3-dimensional image display 24 in such a manner as shown in FIG. 6C (step S309). If the user determines that the cross sections are not displayed (that is, if the answer to step S309 is no), the paracentesis needle insertion path 54 is finally determined.

On the other hand, if the user determines that the cross sections are displayed (that is, if the answer to step S309 is yes), the following steps are performed. That is, in response to the determination, the operation mode is set in a mode in which the temporarily set paracentesis needle insertion path 54 is fixed as a center axis and the movement of the plane cut 43 is limited to rotation about the center axis. In this mode, the user is allowed to adjust the position of the plane cut 43 such that the plane cut 43 passes through a space between costas by rotating the plane cut 43 within the above limitation using the mouse or the like.

When the paracentesis needle insertion path 54 is temporarily set and the orthogonal cross section 63, in which the temporarily set paracentesis needle insertion path 54 (straight line) lies as the line of intersection, is rotated and set as a paracentesis ultrasonic cross section 66, a region of interest (ROI) 62 indicating a region of the ultrasonic cross section depending on the type of the ultrasonic probe used in the medical treatment may be displayed in a superimposed fashion as shown in FIG. 6A.

If the user roughly specifies a paracentesis needle insertion point on the virtual paracentesis ultrasonic cross section 66 by clicking the mouse or the like, then, for example, a broken line is displayed in a superimposed fashion between the specified insertion point and the affected part center 45 to indicate a virtual paracentesis needle 61. Furthermore, in this case, the length of the virtual paracentesis needle 61 in the virtual paracentesis ultrasonic cross section 66 may be displayed on the same screen.

The displaying of the virtual paracentesis needle 61 may be performed such that the paracentesis needle insertion path 54 is automatically displayed when the ultrasonic probe line is set depending on a fixture of the paracentesis needle of the ultrasonic probe to be used in treatment.

Figure 6B:
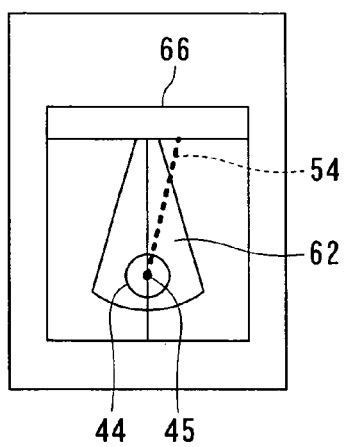
Figure 6C:
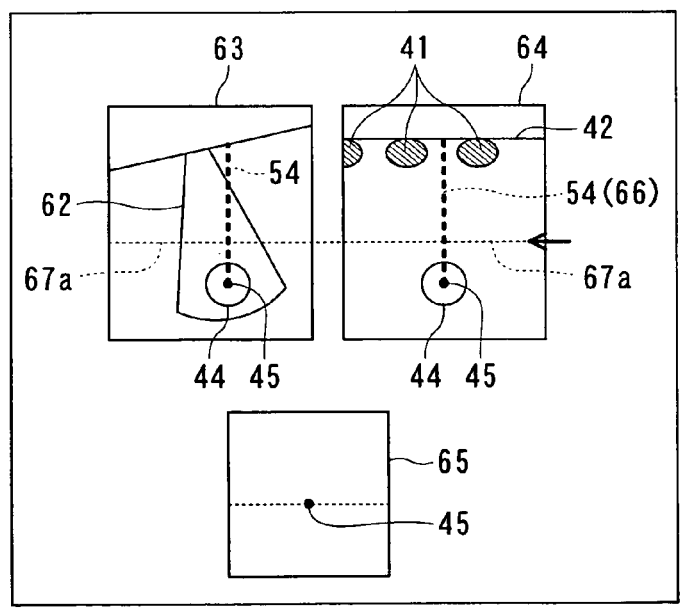

When the position at which to display the virtual paracentesis needle 61 is determined, a volume rendering image including the plane cut 43 may be displayed such that an image of the virtual paracentesis ultrasonic cross section 66 including the ROI 62 is displayed on another screen or in another window, as shown in FIG. 6B.

FIG. 6C shows an example of a manner in which the three orthogonal cross sections set in the above-described manner are displayed on the screen of the 3-dimensional image display 24 (step S310). In the example shown in FIG. 6C, of the two orthogonal cross sections 63 and 64 (FIG. 6A) intersecting each other along the virtual paracentesis needle insertion path 54, the cross section 63 rotated about the paracentesis needle insertion path 54 into a position corresponding to the virtual paracentesis ultrasonic cross section 66 including the ROI is displayed in an upper left area of the screen and the cross section 64, which orthogonally intersects along the paracentesis needle insertion path 54 with the cross section displayed in the upper left area, is displayed in an upper right area of the screen. In a lower area of the screen, the cross section 65 orthogonal to the paracentesis needle insertion path 54 is displayed. In FIG. 6C, a line 67a indicating the position of a cross section 67 perpendicular to the center axis is drawn on the two orthogonal cross sections 63 and 64 sharing the same center line, and the line 67a is displayed in synchronization with the cross sections 63 and 64 orthogonally intersecting each other along the center axis.

In the examination of the paracentesis needle insertion path 54 (in step S310), if no part located too close to the paracentesis needle insertion path 54 is found, the user moves the cursor to the "insertion path determination" button displayed on the screen of the 3-dimensional image display 24 by operating the mouse or the like and clicks the button thereby transmitting a command to the CPU of the image processing/displaying apparatus 15 to employ the current paracentesis needle insertion path 54 as a finally determined paracentesis needle insertion path 54. In response to receiving the command, the CPU transmits a signal to the probe position identification unit 26 to employ the current paracentesis needle insertion path 54 as a finally determined paracentesis needle insertion path 54 (the answer to step S311 becomes yes).

On the other hand, if a part located too close to the paracentesis needle insertion path 54 is found (that is, if the answer to step S311 is no), the paracentesis needle insertion path 54 is turned about the affected part center 45 within the current virtual paracentesis ultrasonic cross section 66 thereby changing the paracentesis needle insertion point 54 from the current point to another point within the same plane cut 43 (thus, the answer to step S312 is no). In this case, under the control of the CPU, the probe position identification unit 26 simultaneously rotates the ROI 62 and the virtual paracentesis needle 61 in the current plane cut 43 in the volume rendering image shown in FIG. 6A, and changes the images shown in FIGS. 6B and 6C in synchronization with the rotation (step S310).

However, if an obstacle (located too close to the paracentesis needle insertion path 54) cannot be avoided by changing the paracentesis needle insertion path 54 within the current virtual paracentesis ultrasonic cross section 66 in the above-described manner (that is, if the answer to step S312 is yes), the CPU, in response to a command issued by the user, commands the probe position identification unit 26 to reset the paracentesis needle insertion path 54 in such a manner as described below. That is, in the volume rendering image including the plane cut 43 shown in FIG. 6A, the plane cut 43 is rotated such that the insertion position of the paracentesis needle comes to a position in another space between costas or to a position below a costal arch, and the position of the virtual paracentesis needle insertion path 54 is set again. That is, the process returns to step S306 to again perform the above-described process from the step of temporarily setting the paracentesis needle insertion point.

As described above, in the present embodiment, when the paracentesis needle insertion path 54 is set in step S308, the paracentesis needle insertion path 54 is displayed in the three orthogonal cross sections, two of which orthogonally intersect each other along the paracentesis needle insertion path 54, thereby making it possible to determine in a highly reliable fashion whether there are no parts located too close to the paracentesis needle insertion path 54.

Modification 1

Figure 7A:
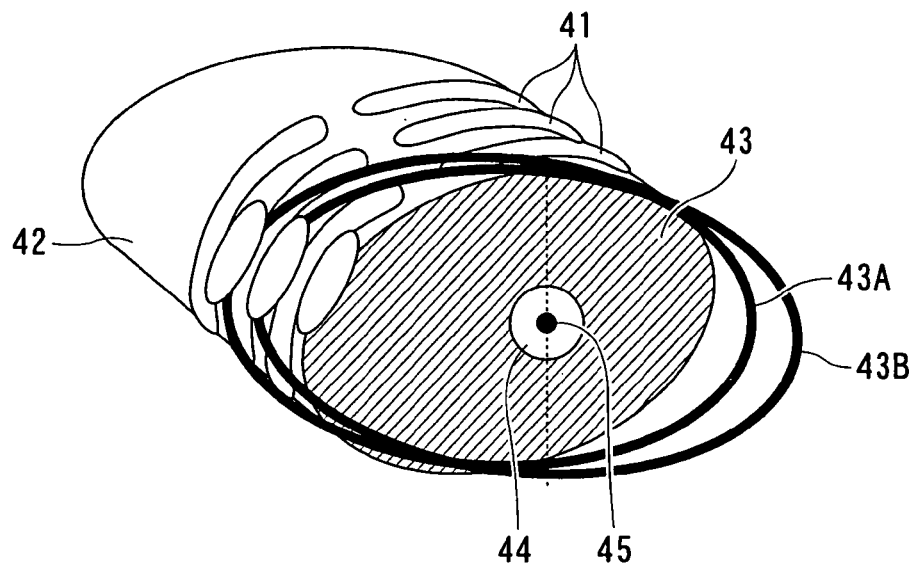
FIG. 7A is a diagram showing an examples of a plurality of plane cuts including a paracentesis needle insertion path.
Figure 7B:
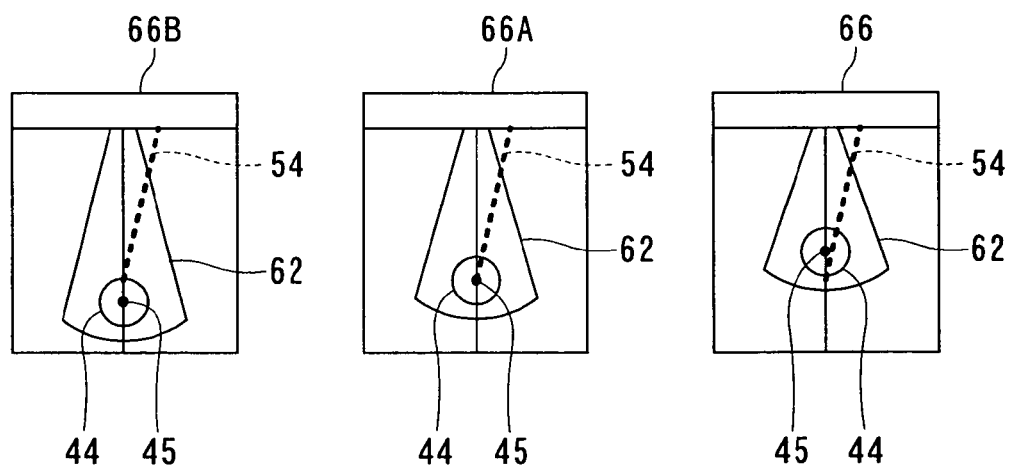
FIG. 7B is a diagram showing virtual paracentesis ultrasonic cross sections.

In stead of a single virtual paracentesis ultrasonic cross section 66 in the above-described manner, virtual paracentesis ultrasonic cross sections 66 corresponding to plane cuts 43 in different positions corresponding to spaces between costas or a point below costal arch may be simultaneously displayed as shown in FIG. 7. That is, as shown in FIG. 7A, when plane cuts 43, 43A and 43B are set by a user such that each plane cut passes through the affected part center 45 and such that respective plane cuts pass through different spaces between costa or a point below a costal arch (corresponding to probe lines), virtual paracentesis ultrasonic cross sections 66, 66A, and 66B corresponding to the respective plane cuts 43, 43A, and 43B are displayed side by side on the screen as shown in FIG. 7B. The user selects a proper one of the virtual paracentesis ultrasonic cross sections 66, 66A, and 66B and sets the paracentesis needle insertion path.

Modification 2

The location of liver varies depending on the breathing phase because the location of a diaphragm varies depending on the breathing phase. More specifically, in abdominal respiration, the diaphragm moves downward in an inspiratory phase and upward in an expiratory phase. Therefore, the location of liver relative to costas in an X-ray CT image taken in a state in which breathing is stopped in the inspiratory phase can be different from the location of liver in a state in which paracentesis treatment is performed using an ultrasonic diagnostic apparatus, because paracentesis treatment is not necessarily performed in the inspiratory phase. For example, the location of the ultrasonic cross section relative to a particular space between costas varies in the range of −1 cm to +1 cm approximately.

Figure 8A:
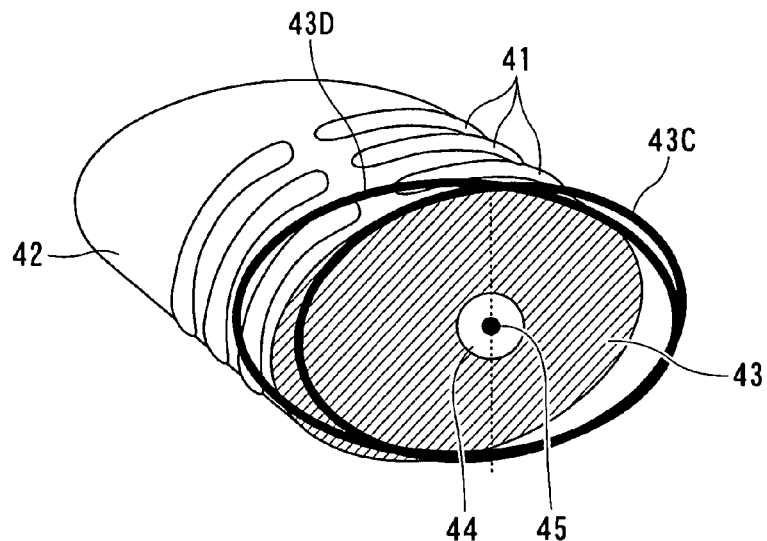
FIG. 8A is a diagram showing an example of a plurality of plane cuts including a paracentesis needle insertion path in respective different breathing phases.
Figure 8B:
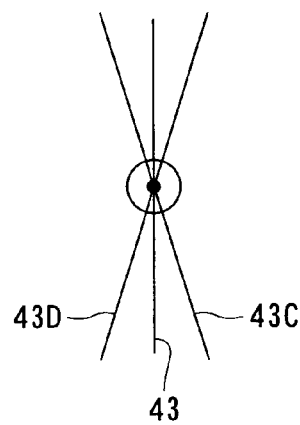
FIG. 8B is a diagram showing relative positions of the plane cuts.
Figure 8C:
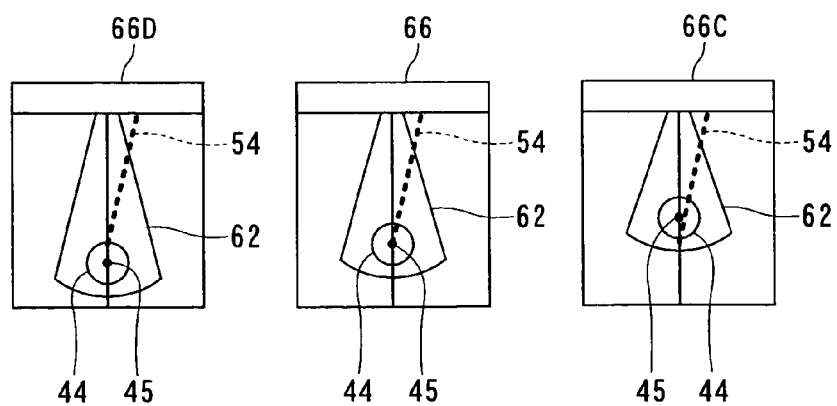
FIG. 8C is a diagram showing virtual paracentesis ultrasonic cross sections corresponding to the respective plane cuts.

In view of the above fact, as shown in FIG. 8, in addition to an initial plane cut 43 and a virtual ultrasonic cross section 66 corresponding thereto, a plurality of plane cuts such as 43C and 43D passing through the affected part center are set at equal angles in opposite directions from the plane cut 43 for example so that the plane cuts pass through difference spaces between costas or a point below a costal arch, taking into account the shift in location of the liver depending on the breathing phase, and virtual ultrasonic cross sections 66, 66C, and 66D corresponding to the respective plane cuts 43, 43C and 43D are displayed side by side on the screen. The user compares the virtual ultrasonic cross sections 66, 66C, and 66D with a real-time image displayed, for example, on the ultrasonic diagnostic apparatus 16 and selects a cross section most suitable for setting a paracentesis needle insertion point.

Displaying a plurality of virtual paracentesis ultrasonic cross sections side by side on the screen is useful in particular to reduce the influence of breathing.

Second Embodiment

A second embodiment of the present invention is described below. In this second embodiment, steps S301 to S305 of the flow chart shown in FIG. 3 are performed in a similar manner to the first embodiment described above. However, after completion of locking the plane cut at a position where the affected part center 45 is in the plane cut 43 in step S305, the following steps of displaying images are performed differently as described below. That is, in the second embodiment, an MPR (Multi Planar Reconstruction) image including three orthogonal cross sections is displayed, and furthermore, one of the three cross sections is displayed in the form of a volume image. The structure of the image processing/displaying apparatus 1 used in the present embodiment is basically similar to that used in the first embodiment, and thus a duplicated description thereof is not given herein.

Some users prefer to use an MPR image rather than a 3-dimensional volume image to find an affected part more easily. The present embodiment of the present invention descried below can meet such a need.

FIG. 9 shows an example of an MPR image of three orthogonal cross sections displayed on the 3-dimensional image display 24, wherein an image of a cross section taken in a certain direction is displayed in area (a) of the screen, an image of a cross screen orthogonally intersecting the cross section displayed in an area (a) along an axis 102 extending in the cross section (a) and through the affected part center 45 is displayed in an area (b), and an image of a cross screen orthogonally intersecting the cross section displayed in the area (a) along an axis 103 extending in the cross section (a) and through the affected part center 45 is displayed in an area (c). An image of a whole chest based on 3-dimensional volume data is displayed as a reference image in an area (d).

The cross sections displayed in the areas (a), (b), and (c) in FIG. 9 are moved in parallel or rotated about the fixed affected part center 45 so that, at least in the cross section shown in the area (a), the end of a single paracentesis needle is displayed at the substantially central point, that is, so that the affected part center 45 is displayed at the substantially central point. In synchronization with the operation of moving or rotating the MPR cross sections, the plane cut 43 in the reference image displayed in the area (d) is updated. In the image displayed in the area (d), an arrow 104 indicating a down-to-up direction or a left-to-right direction in the image displayed in the area (a) is displayed.

In the cross section image shown in the area (a) of FIG. 9, if the user clicks on a point in a 3-dimensional space by using the mouse or the like thereby specifying a treatment center locking point (affected part center 45) at which to put the end of the paracentesis needle, the specified point is locked as in the first embodiment, and the plane cut 43 passing through the affected part center 45 is set by rotating the plane cut 43 (step S305 in FIG. 3).

Figure 10:
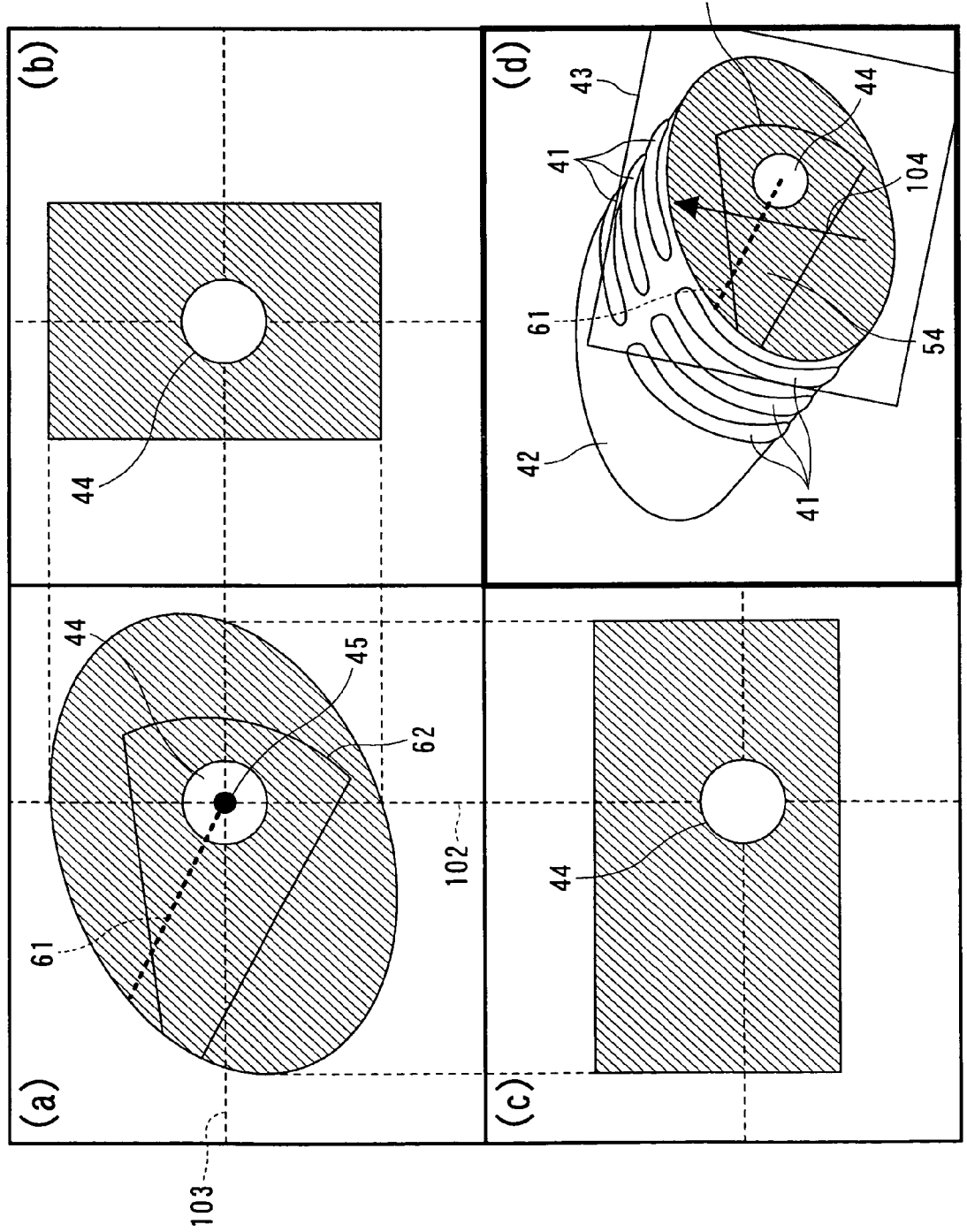
FIG. 10 is a diagram showing an example in which a virtual ultrasonic cross section is determined, and an ROI and a virtual paracentesis needle are added to the image shown in FIG. 9.

Thereafter, in the cross section shown in the area (a) of FIG. 10, rotation about the affected part center 45 is performed, and an ultrasonic probe position is specified thereby determining the virtual ultrasonic cross section 66 as in the first embodiment. Furthermore, as in the first embodiment, an ROI 62 and a virtual paracentesis needle 61 are displayed in a superimposed fashion. In FIG. 10, images displayed in areas (b), (c), and (d) are similar to those displayed in areas (b), (c), and (d) in FIG. 9. The adjustment of the position of the virtual ultrasonic cross section 66 is performed by means of rotation about the affected part center 45.

Figure 11:
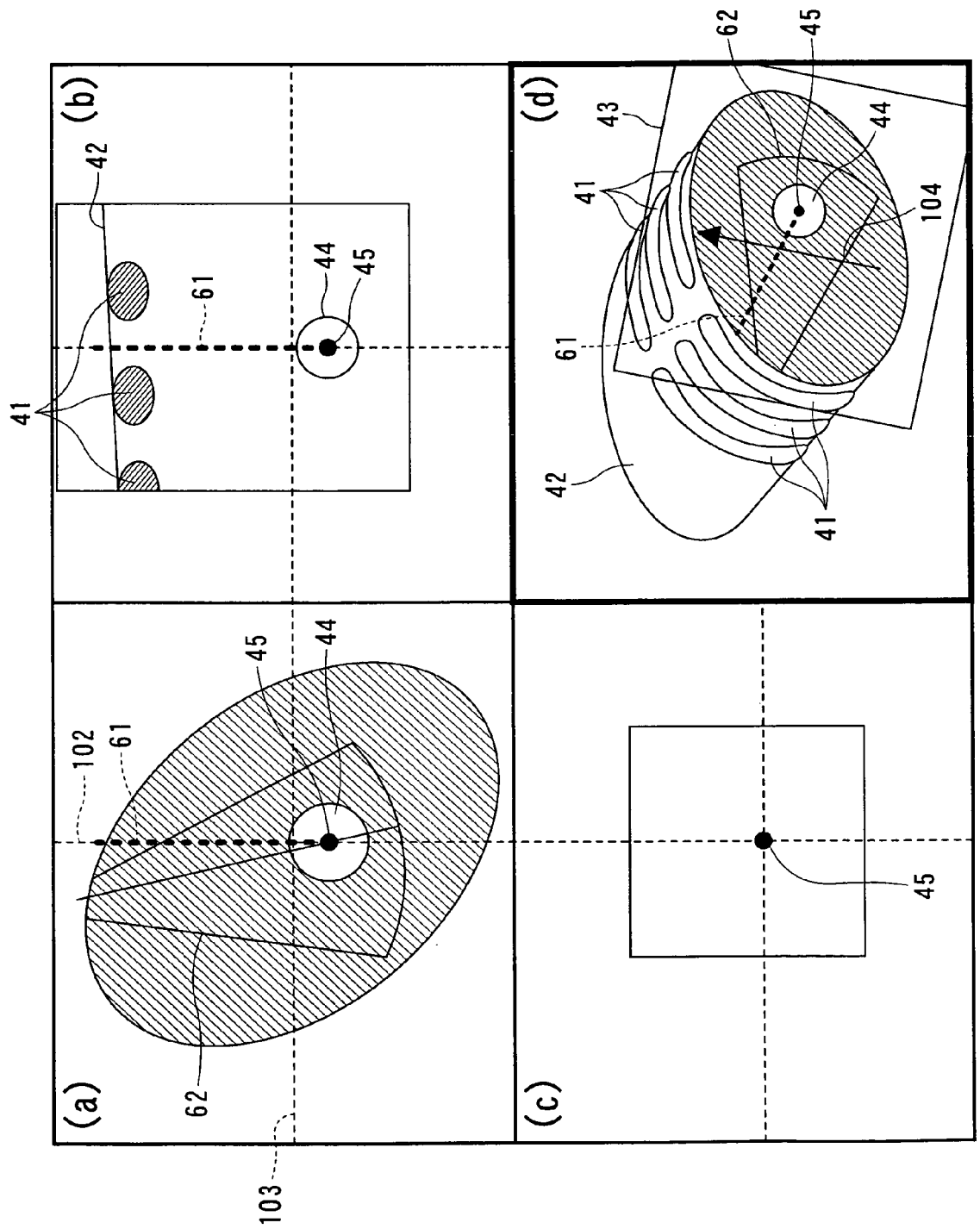
FIG. 11 is a diagram showing an example of an MPR image including a cross section image in which a virtual paracentesis needle extends in a vertical direction.

At the stage where the insertion point of the virtual paracentesis needle 61 has been determined, a cross section image in which the virtual paracentesis needle 61 extends in a vertical direction, a cross section image perpendicular to the plane cut 43 in which the virtual paracentesis needle 61 lies, a cross section image perpendicular to the virtual paracentesis needle 61, and a reference image are displayed in areas (a), (b), (c), and (d), respectively, as shown in FIG. 11 (step S310 in FIG. 3).

Figure 12:
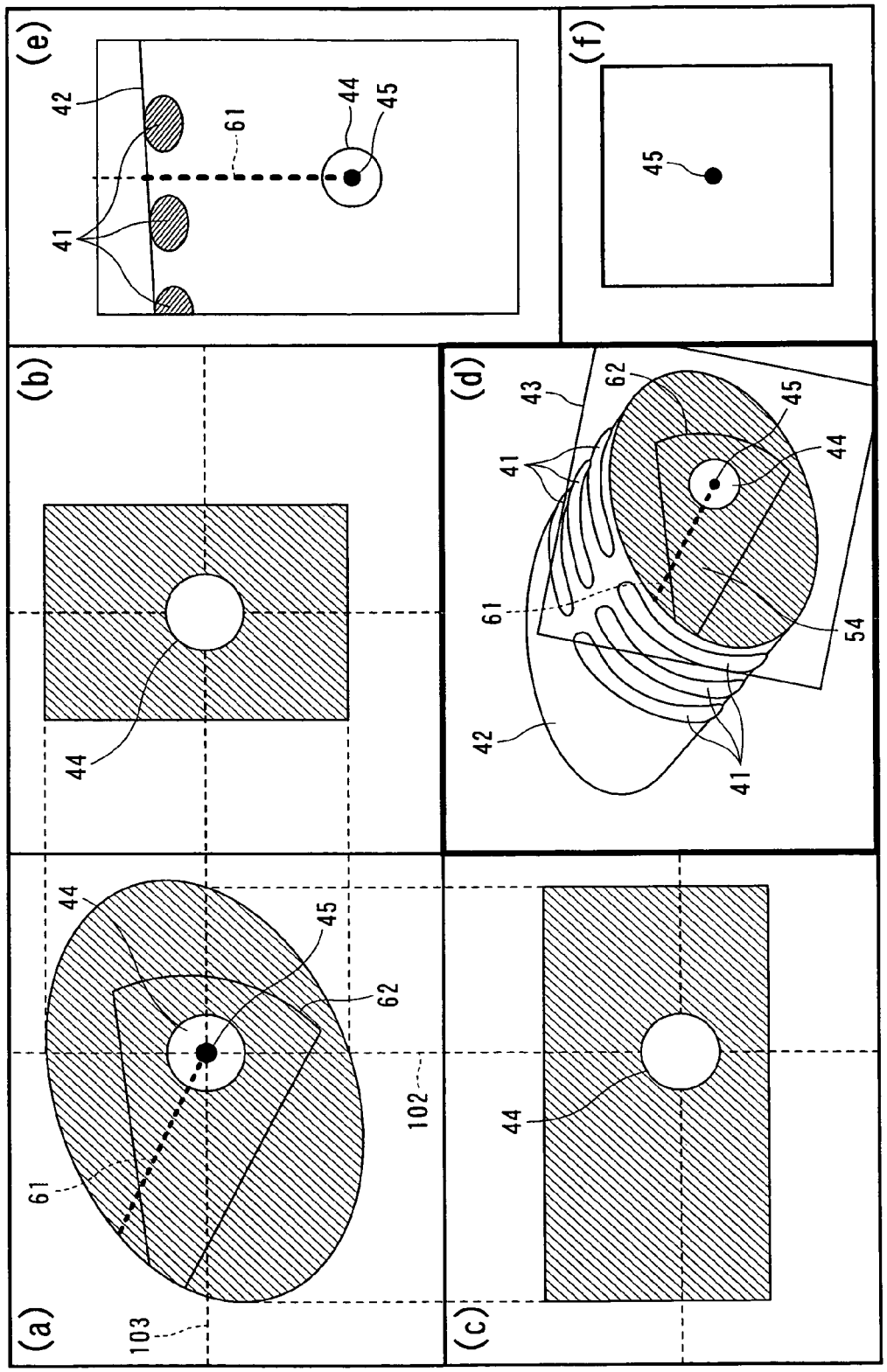
FIG. 12 is a diagram showing an example in which images shown in FIGS. 10 and 11 are displayed side by side on the same screen.

The present embodiment may be modified, for example, as follows. That is, in addition to the three cross section MPR images displayed in the areas (a), (b), and (c) in FIG. 10, as shown in FIG. 12, a cross section image perpendicular to the plane cut 43 in which the virtual paracentesis needle 61 lies is displayed in an area (e) (corresponding to the area (b) in FIG. 11), and a cross section image perpendicular to the virtual paracentesis needle 61 is displayed in an area (f) (corresponding to the area (c) in FIG. 11).

In the present embodiment, as described above, setting of the paracentesis needle insertion path 54 can be performed while viewing the MPR images. This makes it possible to meet various requirements in medical examinations, treatments, or operations.

Third Embodiment

Now, a third embodiment of an image processing/displaying apparatus according to the present invention is described below with reference to the drawings. This third embodiment is different from the first embodiment in that in step S305 of the flow chart shown in FIG. 3, the affected part center 45 is specified in a different manner. The structure of the image processing/displaying apparatus 1 used in the present embodiment is basically similar to that used in the first embodiment, and thus a duplicated description thereof is not given herein.

FIG. 13 shows the manner of specifying the affected part center 45 (that is, the treatment locking point) according to the third embodiment. In the present embodiment, instead of the MPR images of cross sections, a volume rendering display technique capable of setting transparency or a maximum intensity projection, which is also one of image display techniques based on volume rendering, is used to specify the affected part center 45.

In general, an ultrasonic image is low in contrast compared to images obtained by other types of medical diagnostic apparatuses. Because of low contrast, in some cases, an ultrasonic image using volume rendering does not clearly represent a gallbladder, a tumor, a blood vessel, or the like to be observed. The contrast of an ultrasonic projection image can be enhanced by adjusting intensity values associated with voxel values on rays. The method of imaging maximum values of voxel values is known as the maximum intensity projection.

When one volume data is given, the 3-dimensional image generator 23 of the image processing/displaying apparatus 15 performs rendering based on the maximum intensity projection. In the maximum intensity projection, a maximum voxel value of volume data on a ray is employed as a pixel value of a projected image. In general, a voxel corresponding to large echo intensity has a large value. This makes it possible to extract a tissue or a tissue boundary having high echo intensity into a projected image.

Figure 13A:
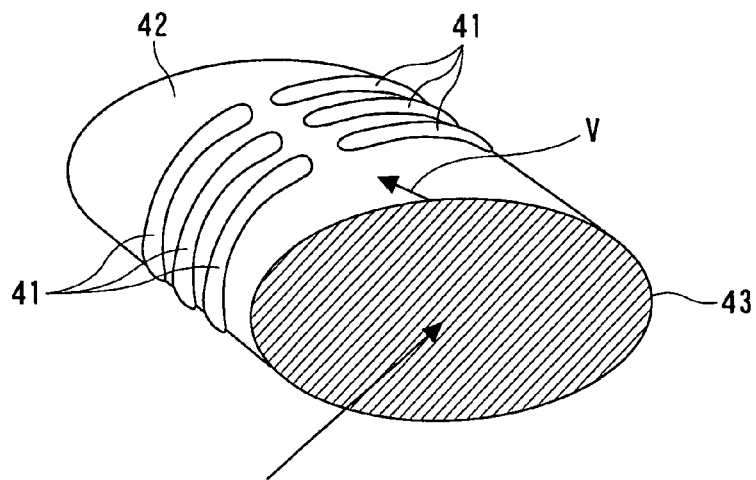
Figure 13B:
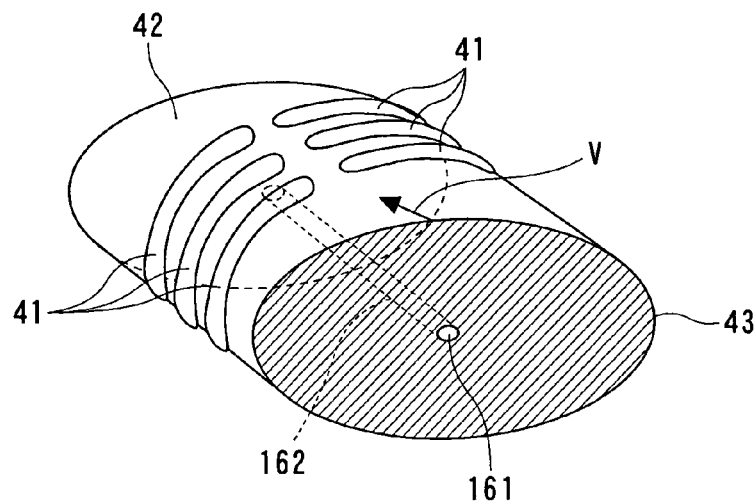

In FIG. 13A, in an image being observed, if a user specifies a treatment center (affected part center 45) by clicking on a point of a part to be treated, the 3-dimensional image generator 23 generates voxel data including graphic data indicating a line 162 with a highest intensity passing through a clicked point and extending in a direction V in which the volume is currently viewed. The resultant generated data is embedded in the original volume data. The specified point 161 is displayed so as to have a highest intensity as shown in FIG. 13B.

Figure 13C:
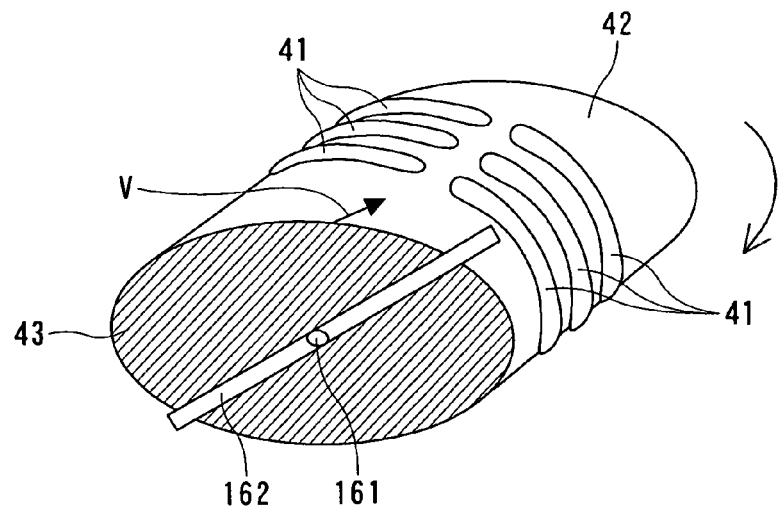

Thereafter, if the resultant volume rendering image is rotated, the graphic line 162 or the highest-intensity line 162 becomes visible as shown in FIG. 13C. In this state, the user again clicks on a point in the 3-dimensional space to specify the center point 45 of the part to be treated.

Alternatively, two volume images viewed in directions different by 90° may be displayed in two windows so that when the user specifies an affected part center 45 in one of two volume images, a graphic line or a highest-intensity line 162 is immediately displayed in the other volume image.

In the present embodiment, as described above, setting of a paracentesis needle insertion path is performed using a maximum intensity projection image or a volume rendering image whose transparency is allowed to be adjusted, and thus it is possible to easily and properly set a paracentesis needle insertion path even in a case in which a part such as a gallbladder, a tumor, or a blood vessel would not be clearly displayed in a conventional volume rendering image using an ultrasonic imaging apparatus or the like.

Fourth Embodiment

Figure 15:
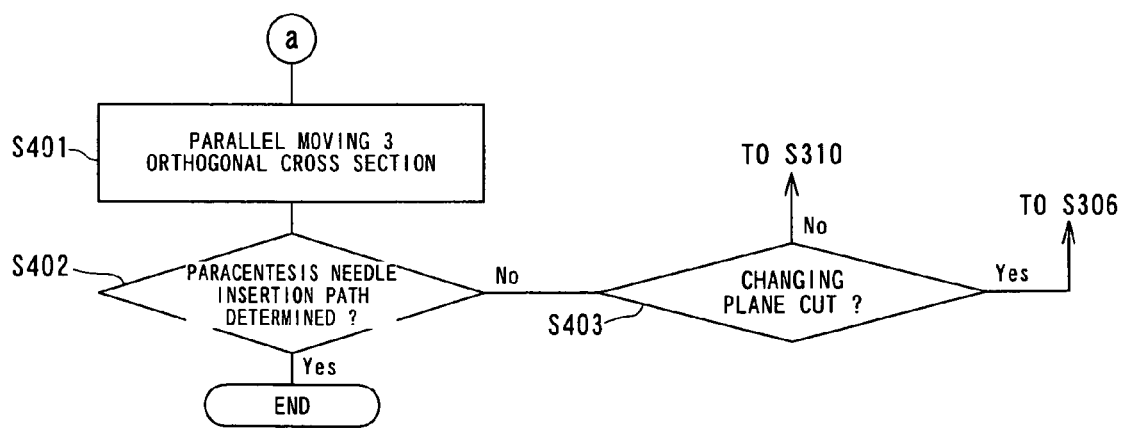
FIG. 15 is a flow chart showing an operation of the image processing/displaying apparatus according to the fourth embodiment of the present invention.

Now, a fourth embodiment of an image processing/displaying apparatus according to the present invention is described below with reference to the drawings. The image processing/displaying apparatus according to the present embodiment is different from that according to the first embodiment in that the process of setting a paracentesis needle insertion path includes additional steps as shown in FIG. 15 for more precisely setting an affected part. The other steps are similar to those according to the first embodiment, and thus they are not described again herein.

Figure 14:
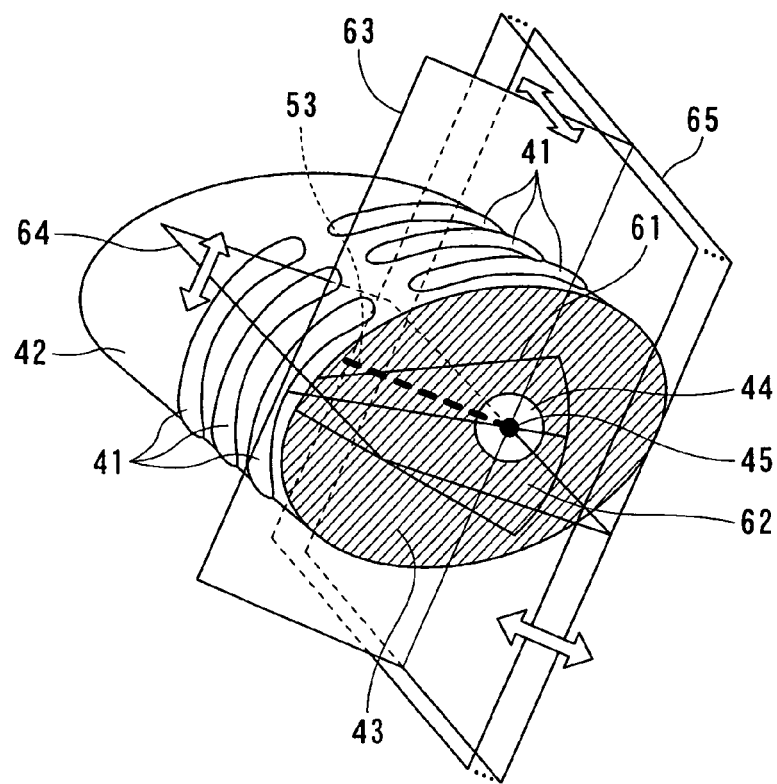
FIG. 14 is a diagram showing a manner in which three orthogonal cross sections, two of which orthogonally intersect each other along a paracentesis needle insertion path, are parallel displaced in an image processing/displaying apparatus according to a fourth embodiment of the present invention.

After displaying three orthogonal cross sections, two of which orthogonally intersect along a paracentesis needle insertion path with each other as shown in FIG. 6A (step S310 in FIG. 3), if a user drags and drops a cross section 65 perpendicular to the center axis by using a mouse or the like, the CPU commands the probe position identification unit 26 to parallel move the cross section 65 perpendicular to the center axis by an amount corresponding to the amount of dragging, along the paracentesis needle insertion path 54 within the range from the affected part center 45 to the paracentesis needle insertion point, as shown in FIG. 14 (step S401).

The user observes the image while parallel moving the cross section 65 perpendicular to the center axis to determine whether there is a part such as a lung, a diaphragm, or a blood vessel that should be avoided from the paracentesis needle insertion path 54. Each of the two orthogonal cross sections 63 and 64 orthogonally intersecting along the virtual paracentesis needle insertion path 54 with each other is also parallel moved in a similar manner to examine whether there is a part such as a lung, a diaphragm, or a blood vessel that should be avoided from the paracentesis needle insertion path 54.

When the paracentesis needle insertion path 54 is examined in the above-described manner (in step S401), if no part located too close to the paracentesis needle insertion path 54 is found, the user moves the cursor to the "insertion path determination" button displayed on the screen of the 3-dimensional image display 24 by operating the mouse or the like and clicks the button thereby transmitting a command to the CPU of the image processing/displaying apparatus 15 to employ the current paracentesis needle insertion path 54 as a finally determined paracentesis needle insertion path 54. In response to receiving the command, the CPU transmits a signal to the probe position identification unit 26 to employ the current paracentesis needle insertion path 54 as a finally determined paracentesis needle insertion path 54 (the answer to step S402 becomes yes).

On the other hand, if a part located too close to the paracentesis needle insertion path 54 is found (that is, if the answer to step S402 is no), the paracentesis needle insertion path 54 is turned about the affected part center 45 within the current virtual paracentesis ultrasonic cross section 66 thereby changing the paracentesis needle insertion point 54 from the current point to another point within the same plane cut 43 (thus, the answer to step S403 is no). In this case, under the control of the CPU, the probe position identification unit 26 simultaneously rotates the ROI 62 and the virtual paracentesis needle 61 in the current plane cut 43 in the volume rendering image shown in FIG. 6A, and changes the images shown in FIGS. 6B and 6C in synchronization with the rotation (step S310).

However, if an obstacle (located too close to the paracentesis needle insertion path 54) cannot be avoided by changing the paracentesis needle insertion path 54 within the current virtual paracentesis ultrasonic cross section 66 in the above-described manner (that is, if the answer to step S402 is yes), the CPU, in response to a command issued by the user, commands the probe position identification unit 26 to reset the paracentesis needle insertion path 54 in such a manner as described below. That is, in the volume rendering image including the plane cut 43 shown in FIG. 6A, the plane cut 43 is rotated such that the insertion position of the paracentesis needle comes to a position in another space between costas or to a position below a costal arch, and the position of the virtual paracentesis needle insertion path 54 is set again. That is, the process returns to step S306 in FIG. 3 to again perform the above-described process from the step of temporarily setting the paracentesis needle insertion point.

Figure 16:
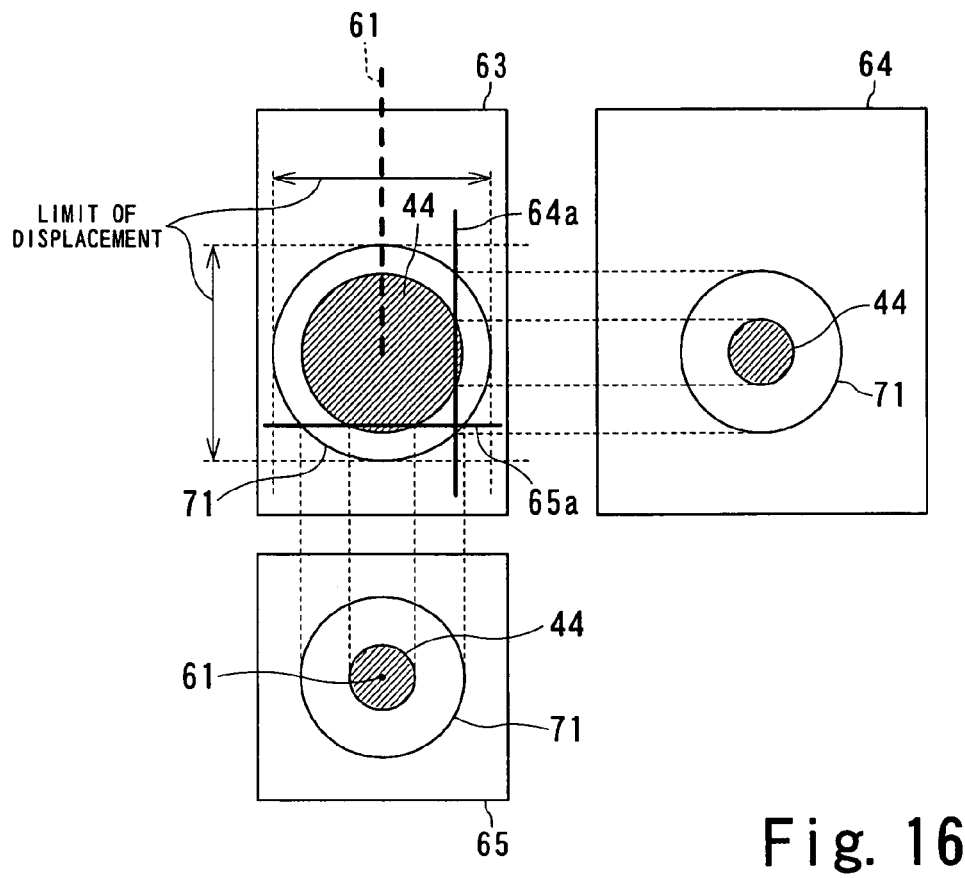
FIG. 16 is a diagram showing an example of a manner in which an affected part is viewed when the three orthogonal cross sections are parallel displaced and also showing ranges of the parallel displacement.

When one or more of the orthogonal three cross sections are parallel displaced in predetermined ranges, the image of the affected part 44 in each cross section varies as described below. FIG. 16 shows images of the affected part 44 in the cross sections 63 and 64 orthogonally intersecting along the virtual paracentesis needle insertion path with each other and in the cross section 65 perpendicular to the intersection line of the cross sections 63 and 64 (FIG. 6C), wherein the images are shown in an enlarged fashion.

In the specific example shown in FIG. 16, the cross section 63 orthogonally intersecting along the virtual paracentesis needle insertion path with the cross section 64 remains in its original position without being parallel displaced, and thus the cross section 63 passes through the affected part center 45, that is, the image of the affected part 44 in the cross section 63 has a maximum size. On the other hand, in the cross section 64 orthogonally intersecting along the virtual paracentesis needle insertion path with the cross section 63 and in the cross section 65 perpendicular to the intersection line of the cross sections 63 and 64, the sizes of the images in those cross sections 64 and 65 are smaller than those obtained when the cross sections 64 and 65 pass through the center 45 of the affected part, because the cross sections 64 and 65 are in parallel displaced positions 64a and 65a.

In the respective virtual ultrasonic cross sections, images of cross sections of a spherical shell (indicating an ablation region) 71 whose center is located at the affected part center 45 and which has a greater size than the size of the affected part 44 are displayed in a superimposed fashion. The size of the sphere shell 71 in each cross section is determined from a specified value indicating the diameter, the radius, or the volume and varied in synchronization with parallel displacement of each cross section. The displaying of the sphere shell 71 makes it possible for a user to recognize the RF ablation range.

The ranges of parallel displacement of the respective orthogonal cross sections may be limited to the diameter of the spherical shell 71. This prevents the orthogonal three cross sections from moving by unnecessarily large amounts. Although in the present embodiment, the ranges within which the respective cross sections are allowed to be parallel displaced are set to values corresponding to the size of the spherical shell 71, the ranges are not necessarily needed to be set to such values. For example, the ranges may be set to values depending on the shape, such as a cube, a rectangular parallelepiped, or a fusiform, of the affected part 44.

The RF ablation region is three-dimensionally examined in a mode in which, as shown in FIG. 16, the virtual ultrasonic cross sections are allowed to be parallel displaced within the ranges in which each cross section intersects the sphere. As each virtual ultrasonic cross section is parallel displaced, the size of the spherical shell in the cross section varies depending on the position at which the sphere 71 is passed through by the cross section. If the affected part center 45 is moved along the virtual paracentesis needle insertion path 54, the image of the 3-dimensional RF ablation region is varied in synchronization with the movement of the affected part center 45. When the cross section perpendicular to the virtual paracentesis path is in a position where the cross section passes through affected part center, the affected part center 45 in the cross section perpendicular to the virtual paracentesis axis may also be updated in synchronization with the parallel displacement.

In the case in which the paracentesis needle insertion path is set using the MPR image according to the second embodiment described above, the sphere 71 indicating the range to be treated may be specified in the above-described manner and may be displayed in the screen areas (a), (b), and (c) shown in FIG. 11 in a superimposed fashion.

As described above, in addition to the functions and advantages according to the first embodiment described above, the present embodiment provides the capability of displaying images while parallel displacing the cross sections orthogonally intersecting along the paracentesis needle insertion path 54 with each other and the cross section perpendicular to the paracentesis needle insertion path 54. This makes it possible to determine in a still more reliable fashion whether there is a part that should be avoided from the paracentesis needle insertion path 54.

Fifth Embodiment

A fifth embodiment of an image processing/displaying apparatus according to the present invention is described below with reference to the drawings. The image processing/displaying apparatus 15 according to the present embodiment is different from that according to the first embodiment in that after a paracentesis needle insertion path is set, an image indicating a body surface is superimposed on a 3-dimensional image similar to that according to the first embodiment. The other steps are similar to those according to the first embodiment, and thus they are not described again herein.

Figure 17:
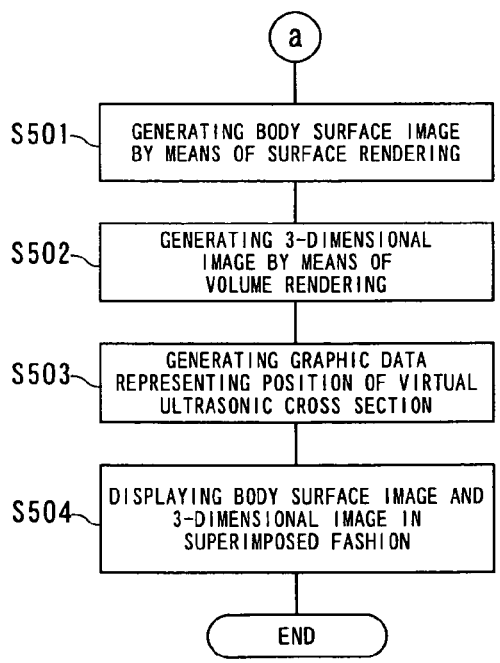
FIG. 17 is a flow chart showing an operation of an image processing/displaying apparatus according to a fifth embodiment of the present invention.

FIG. 17 is a flow chart showing an operation of the image processing/displaying apparatus 15 according to the fifth embodiment of the present invention. After the paracentesis needle insertion path is finally determined (the answer to step S311 in FIG. 3 is yes), if a button on an operation control panel (not shown) or a key on a keyboard (not shown) of the input unit 27 of the image processing/displaying apparatus 15 is pressed, the 3-dimensional data reconstruction unit 22 of the image processing/displaying apparatus 15 generates an image indicating only a body surface of a subject by means of surface rendering from volume image data (step S501). Then in step S502, the 3-dimensional data reconstruction unit 22 generates a 3-dimensional image representing the position and the shape of each bone of the subject by means of volume rendering.

In step S503, the 3-dimensional data reconstruction unit 22 generates graphic data graphically representing the position of the virtual ultrasonic cross section and the shape of a paracentesis needle.

Figure 18A:
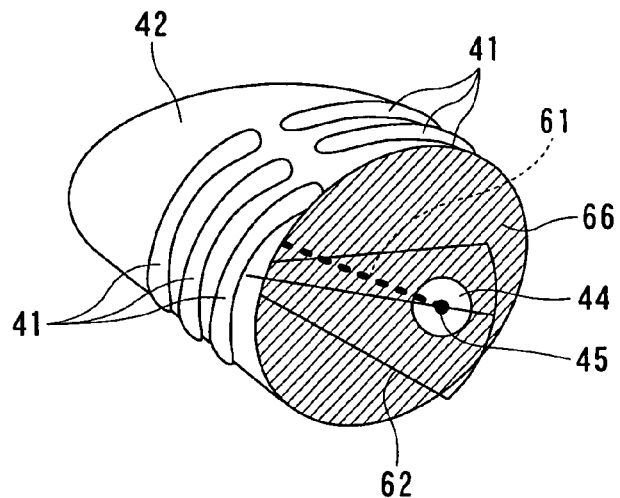
FIG. 18A is a diagram showing a 3-dimensional image obtained by means of volume rendering.
Figure 18B:
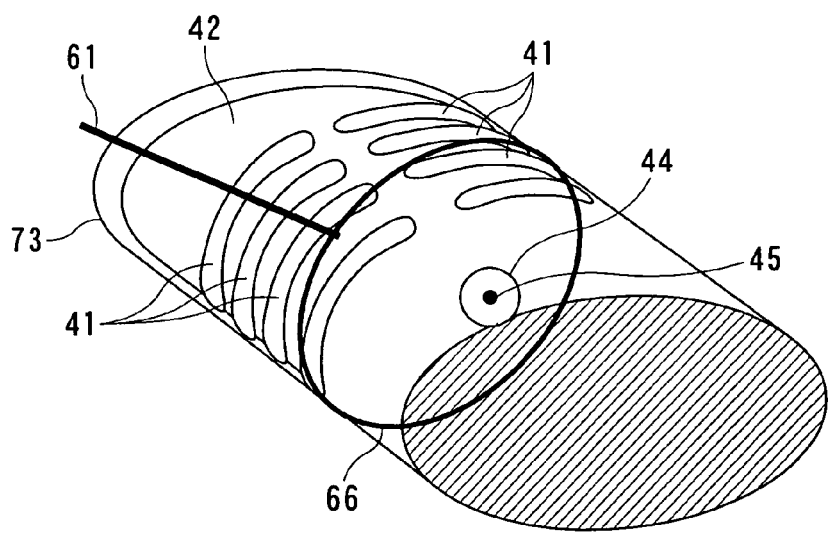
FIG. 18B is a diagram showing a body surface image obtained by means of surface rendering and a graphical image indicating the position of a virtual ultrasonic cross section superimposed on the image shown in FIG. 18A.

In step S504, the body surface image and the 3-dimensional image are displayed in a superimposed fashion. In FIG. 18A, reference numeral 61 denotes a virtual paracentesis needle and 66 denotes a virtual ultrasonic cross section. From the image shown in FIG. 18A, an image of a body surface 73 and an image representing the positions and shapes of bones 41 are generated and displayed together with the images of the virtual ultrasonic cross section 66 and the virtual paracentesis needle 61 as shown in FIG. 18B.

Figure 19A:
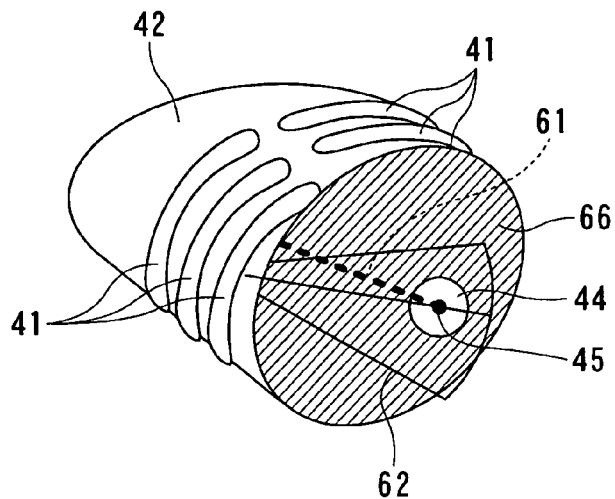
FIG. 19A is a diagram showing a 3-dimensional image obtained by means of volume rendering.
Figure 19B:
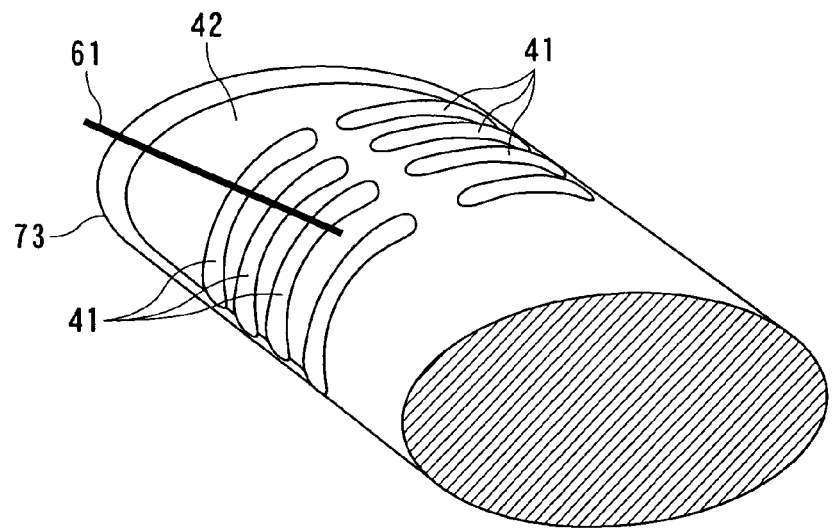
FIG. 19B is a diagram showing a body surface image obtained by means of surface rendering superimposed on the image shown in FIG. 19A.

In a case in which the displaying of the virtual ultrasonic cross section 66 and/or the paracentesis needle 61 makes it difficult to view the other parts of the image, the virtual ultrasonic cross section 66 and/or the paracentesis needle 61 may not be displayed. FIG. 19A shows a 3-dimensional image including a virtual paracentesis needle 61 and a virtual ultrasonic cross section 66 in a similar manner as in FIG. 18A. FIG. 19B shows an example in which the images of the virtual ultrasonic cross section 66 and the affected part 44 are deleted although the virtual paracentesis needle 61 remains.

In the present embodiment described above, the position of the virtual ultrasonic cross section 66 is displayed after the insertion point of the paracentesis needle 61 is finally determined. Alternatively, before the insertion point of the paracentesis needle 61 is finally determined, for example, after first-time setting of the paracentesis needle insertion path is performed in step S308 of the flow chart shown in FIG. 3, the virtual ultrasonic cross section 66 and/or the virtual paracentesis needle 61 may be displayed in synchronization with the 3-dimensional image, in a similar manner as described above with reference to FIG. 18.

By displaying the virtual ultrasonic cross section 66 and/or the virtual paracentesis needle 61 during the process of determining the paracentesis needle insertion point, it becomes possible for the user to recognize at what position the paracentesis will be inserted. The body surface image may also be displayed in synchronization with the 3-dimensional image.

Figure 20:
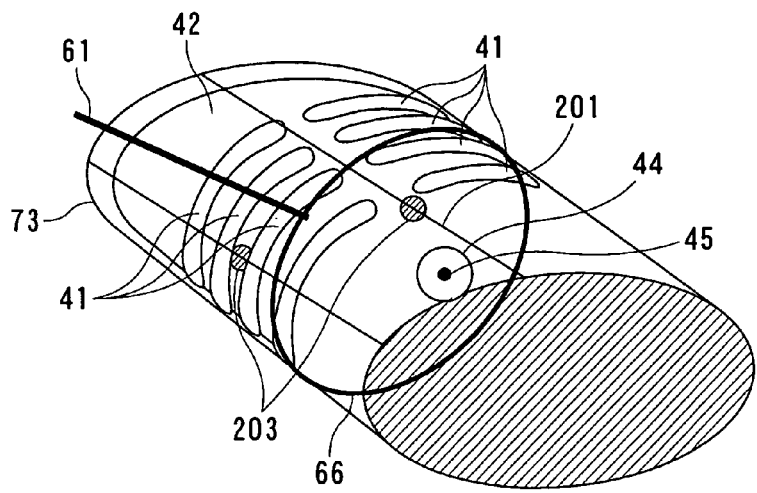
FIG. 20 is a diagram showing a manner of displaying a center line of a subject, in an image processing/displaying apparatus according to a modification of the fifth embodiment of the present invention.

Furthermore, as shown in FIG. 20, the contour of the body surface may be extracted. If the user specifies, using a pointing device such as a mouse, for example, a xiphisternum or a point in a seventh or eighth space between costas and on a middle axillary line, as an anatomical index mark indicating a breast bone or a costa on the basis of the information associated with the extracted contour, the index mark 202 on the body surface and a center line 201 passing through the index mark 202 may be displayed. Furthermore, the distance along a curved line between the index mark 202 and the paracentesis needle insertion point may be automatically measured and the result may be displayed.

Figure 21:
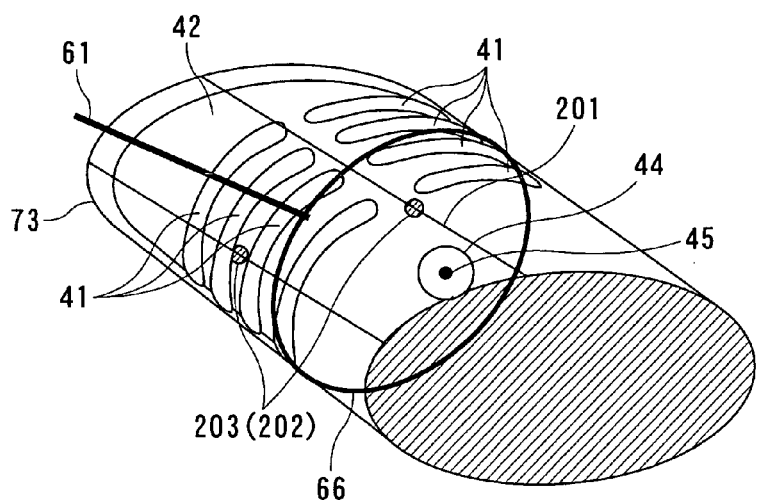
FIG. 21 is a diagram showing a manner of displaying a center line of a patient's body and a mark on a body surface, in an image processing/displaying apparatus according to another modification of the fifth embodiment of the present invention.

Furthermore, as shown in FIG. 21, a landmark 203 depending on the imaging method such as CT or MRI may be put, as an anatomical index mark indicating a breast bone or a costa, at a xiphisternum or a point in a seventh or eighth space between costas and on a middle axillary line, and a CT or MRI image may be taken. The marker 203 may be automatically detected from the CT value or the like, and the index mark 202 on the body surface and center lines 201 passing through the index marks 202 may be displayed. Furthermore, the distance along a curved line between the index mark 202 and the paracentesis needle insertion point may be automatically measured and the result may be displayed.

Figure 22:
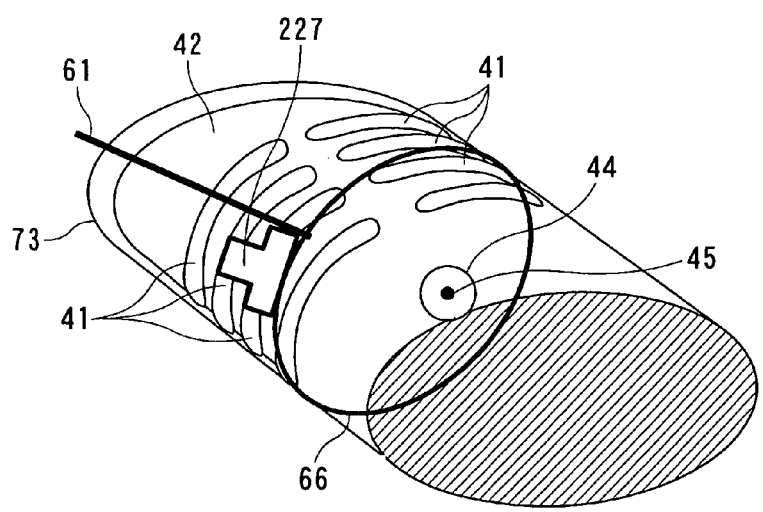
FIG. 22 is a diagram showing an example of a manner of displaying a graphical image of a paracentesis probe superimposed on a body surface image.

A graphical image 227 of ultrasonic probe, such as a figure or a picture, may be superimposed on the body surface image acquired by means of surface rendering and displayed on the 3-dimensional image display 24 as shown in FIG. 22.

For this purpose, the image processing/displaying apparatus further comprises a probe graphic storage unit configured to store a graphical image representing a paracentesis probe and physical relationship between the paracentesis probe and a paracentesis needle. The 3-dimensional image display 24 displays the graphical image representing a paracentesis probe at the location where the paracentesis probe touches body surface and where plane cut 43 intersect the body surface of the body surface image so as to be superimposed on the body surface image generated by the body surface image generating unit.

More specifically, in the case that a line on which to put the paracentesis probe is set on a body surface in the body surface image, similar to the line 51 shown on FIGS. 5A and 5B for example, a graphical image 227 representing a paracentesis probe is displayed at the location, obtained from the probe graphic storage unit, where the paracentesis probe touches the body surface.

In the case that a ROI is set in the plane cut 43, similar to the ROI 61 shown on FIGS. 6A and 6B for another example, a graphical image 227 representing a paracentesis probe is displayed at the location, obtained from the probe graphic storage unit, where the radiation center of the ROI touches the body surface.

In the present embodiment, as described above, a 3-dimensional image obtained by means of volume rendering, a body surface image obtained by means of surface rendering, and a graphic image indicating the position of a virtual ultrasonic cross section are displayed in an superimposed fashion, thereby making it possible for a user to more intuitively recognize a paracentesis needle insertion point.

Sixth Embodiment

A sixth embodiment of an image processing/displaying apparatus according to the present invention is described below with reference to the drawings. In the present embodiment, unlike the previous embodiments in which the image processing/displaying apparatus is assumed to be used mainly in planning of paracentesis, the image processing/displaying apparatus 15 is assumed to be used during paracentesis treatment. The other parts are similar to those in the first embodiment, and similar parts are denoted by similar reference numerals and are not described in further detail herein.

That is, in the image processing/displaying apparatus 15 according to the present embodiment, a virtual ultrasonic cross section and a live ultrasonic image are displayed on the screen of the ultrasonic diagnostic apparatus 16 so that a user can view the virtual ultrasonic cross section at a time immediately before starting paracentesis or during paracentesis.

Figure 23:
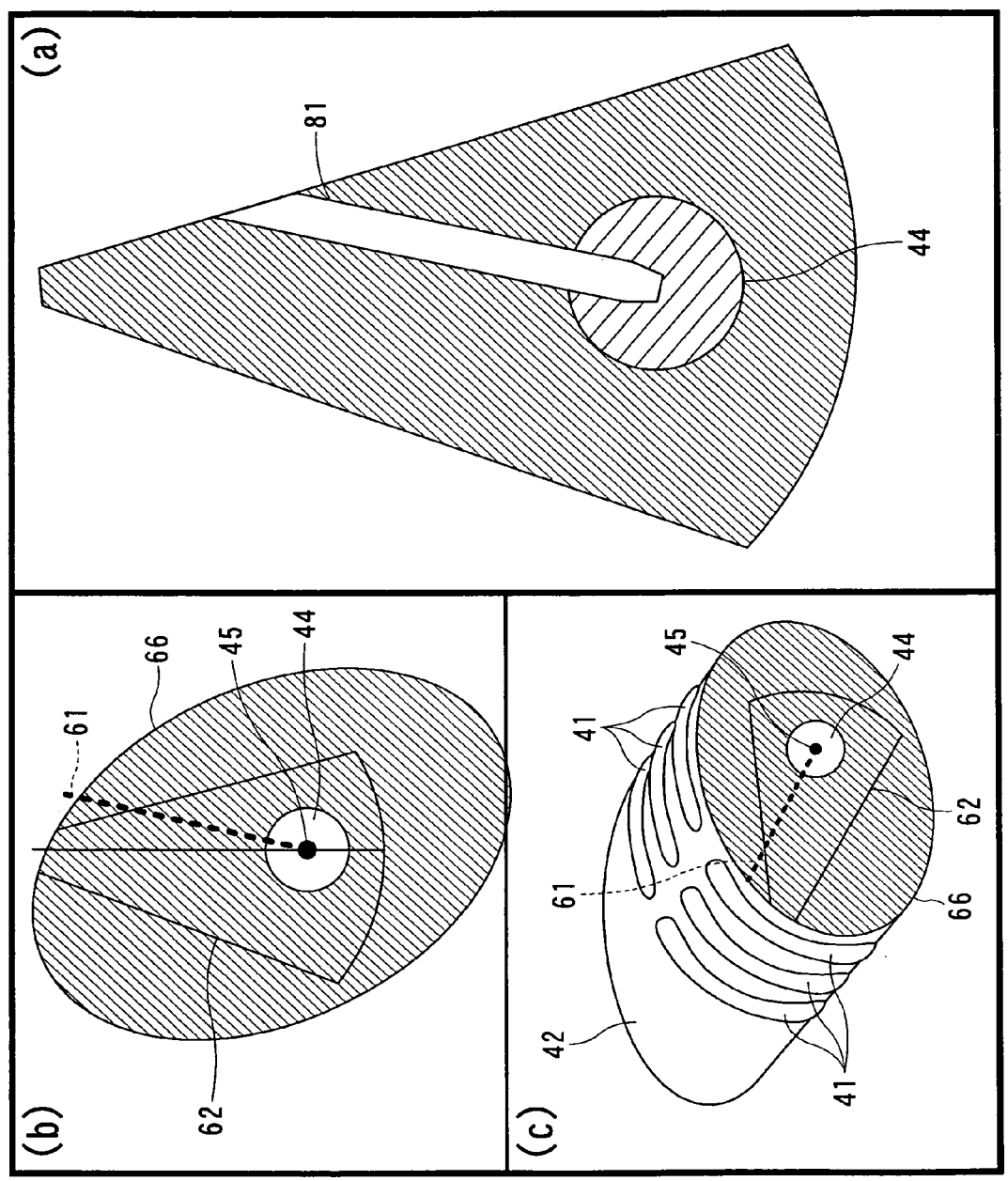
FIG. 23 is a diagram showing an example of a manner in which a live ultrasonic image, an image of a virtual ultrasonic cross section in paracentesis, and a reference image obtained by means of CT volume rendering are displayed, in the image processing/displaying apparatus according to the fifth embodiment of the invention.

As shown in FIG. 23, one screen is divided into two parts: a right-hand part and a left-hand part. A live ultrasonic image (a) is displayed on the right-hand side. On the left-hand side, images obtained in planning of paracentesis are displayed. For example, an image of a virtual ultrasonic cross section (b) obtained according to one of the previous embodiments is displayed in an upper area on the left-hand side and a reference image (c) on CT volume rendering is displayed in a lower area on the left-hand side. The live ultrasonic image includes an image of an actual affected part 44 and an image of an actual paracentesis needle 81.

Figure 24:
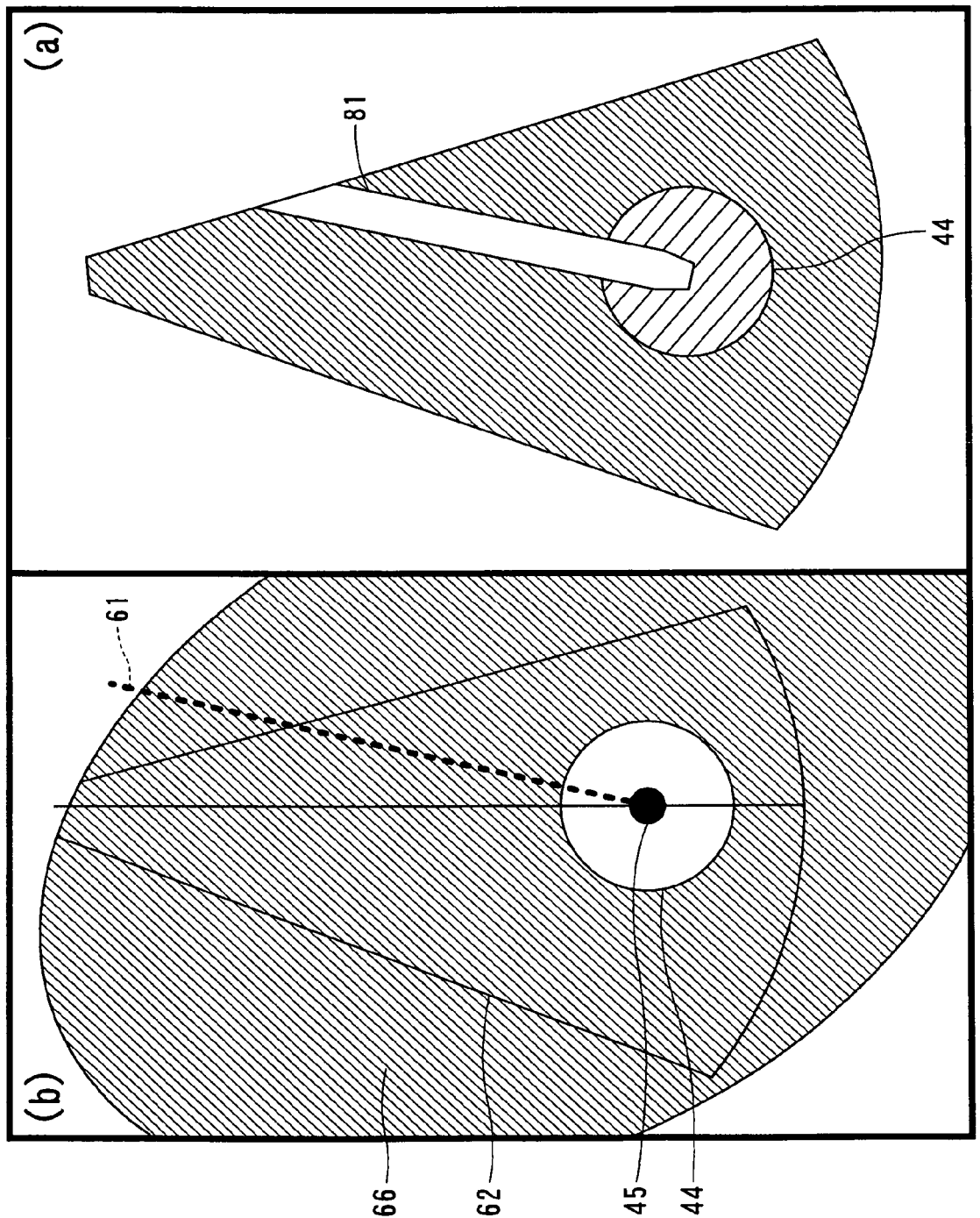
FIG. 24 is a diagram showing an example of a manner in which a live ultrasonic image and an image of a virtual ultrasonic cross section in paracentesis are displayed, in the image processing/displaying apparatus according to the fifth embodiment of the invention.

Alternatively, instead of displaying images in three sub-screens as shown in FIG. 23, images may be displayed in two sub-screens as shown in FIG. 24. More specifically, a live ultrasonic image (a) is displayed in a right-hand subscreen, and an image of a virtual ultrasonic cross section (b) with the same scaling factor as that of the live image displayed in the right-hand subscreen is displayed in a left-hand subscreen. In a state in which both the live image (a) and the image of the virtual ultrasonic cross section (b) are displayed in the right-hand and left-hand subscreens, at a time immediately starting paracentesis, the live image is frozen when it represents a predicted paracentesis needle insertion path and the image of the virtual ultrasonic cross section substantially equal to the frozen image of the cross section is displayed in the left-hand subscreen.

In a case in which paracentesis is performed a plurality of times, the live image is frozen when paracentesis is being performed for a first time, and a next insertion point is determined. If an image of a virtual ultrasonic cross section substantially identical to the frozen cross section image is obtained, freezing is released.

The simultaneous displaying of the image of the virtual ultrasonic cross section and the live image in the above-described manner during paracentesis treatment, makes it possible for a user to determine whether the paracentesis needle is being inserted correctly along the planned path or whether the planned paracentesis needle insertion path is correct.

Seventh Embodiment

Figure 25:
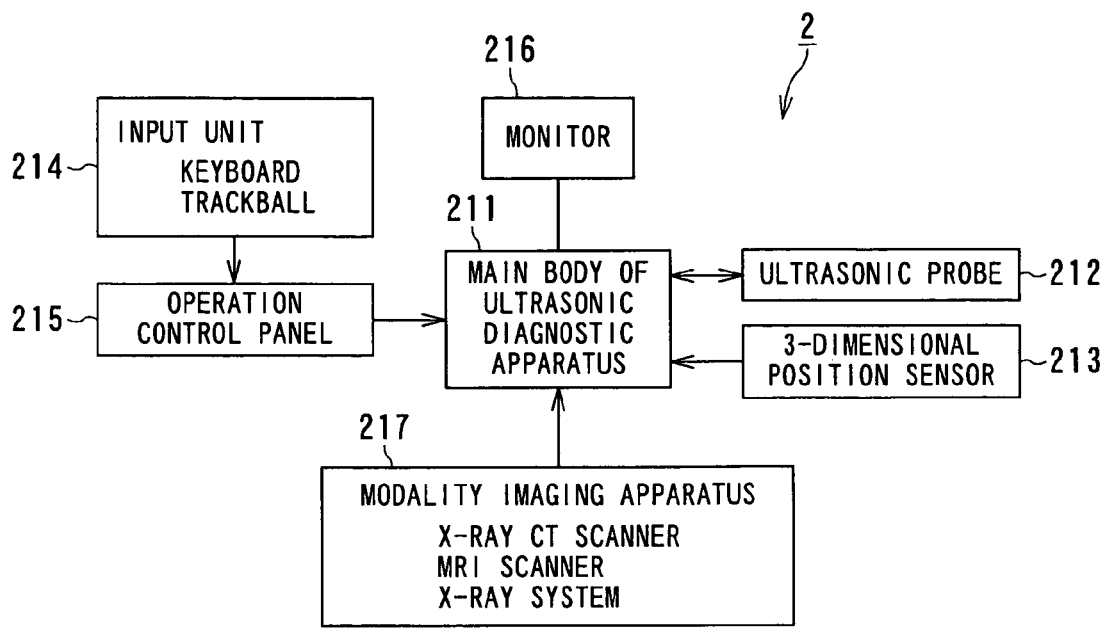
FIG. 25 is a block diagram showing an ultrasonic-imaging diagnostic system including an image processing/displaying apparatus according to a sixth embodiment of the present invention.

A seventh embodiment of an image processing/displaying apparatus according to the present invention is described below with reference to the drawings. FIG. 25 is block diagram showing an ultrasonic-imaging diagnostic system 2 according to the seventh embodiment of the invention.

A main part 211 of an ultrasonic diagnostic apparatus has the capability of processing an image and displaying the resultant image in addition to the capability of taking an ultrasonic image by transmitting and receiving an ultrasonic wave. An ultrasonic probe 212, a 3-dimensional position sensor 213 installed on the ultrasonic probe 212, and an input unit 214 including a keyboard and a trackball or the like and an operation control panel 215 are connected to the main part 211. An ultrasonic image and other modality image are displayed on a monitor 216.

As for the ultrasonic probe 212, a one-dimensional array probe of a widely used type, a mechanical 4D probe capable of detecting a plurality of ultrasonic cross sections by mechanically oscillating a one-dimensional array probe, or a real-time 3D probe using a 2D array may be used.

3-dimensional volume data associated with a 3-dimensional region including an affected part to be treated is acquired using a modality imaging apparatus 217 such as an X-ray computerized tomography (CT) scanner, a magnetic resonance imaging (MRI) scanner, or an X-ray system. The acquired data is described in a format such as DICOM and directly transmitted to the main part 211 of the ultrasonic diagnostic apparatus or indirectly via a DICOM server or the like. The acquired data may also be input to the main part 211 of the ultrasonic diagnostic apparatus using a storage medium such as a CD-R.

The main part 211 of the ultrasonic diagnostic apparatus, the ultrasonic probe 212, the 3-dimensional position sensor 213, the input unit 214, the operation control panel 215 and the monitor 216 constitute the image processing/displaying apparatus of the present invention, and the process described below is executed under the control of the unshown CPU in the main part 211 of the ultrasonic diagnostic apparatus.

Figure 26:
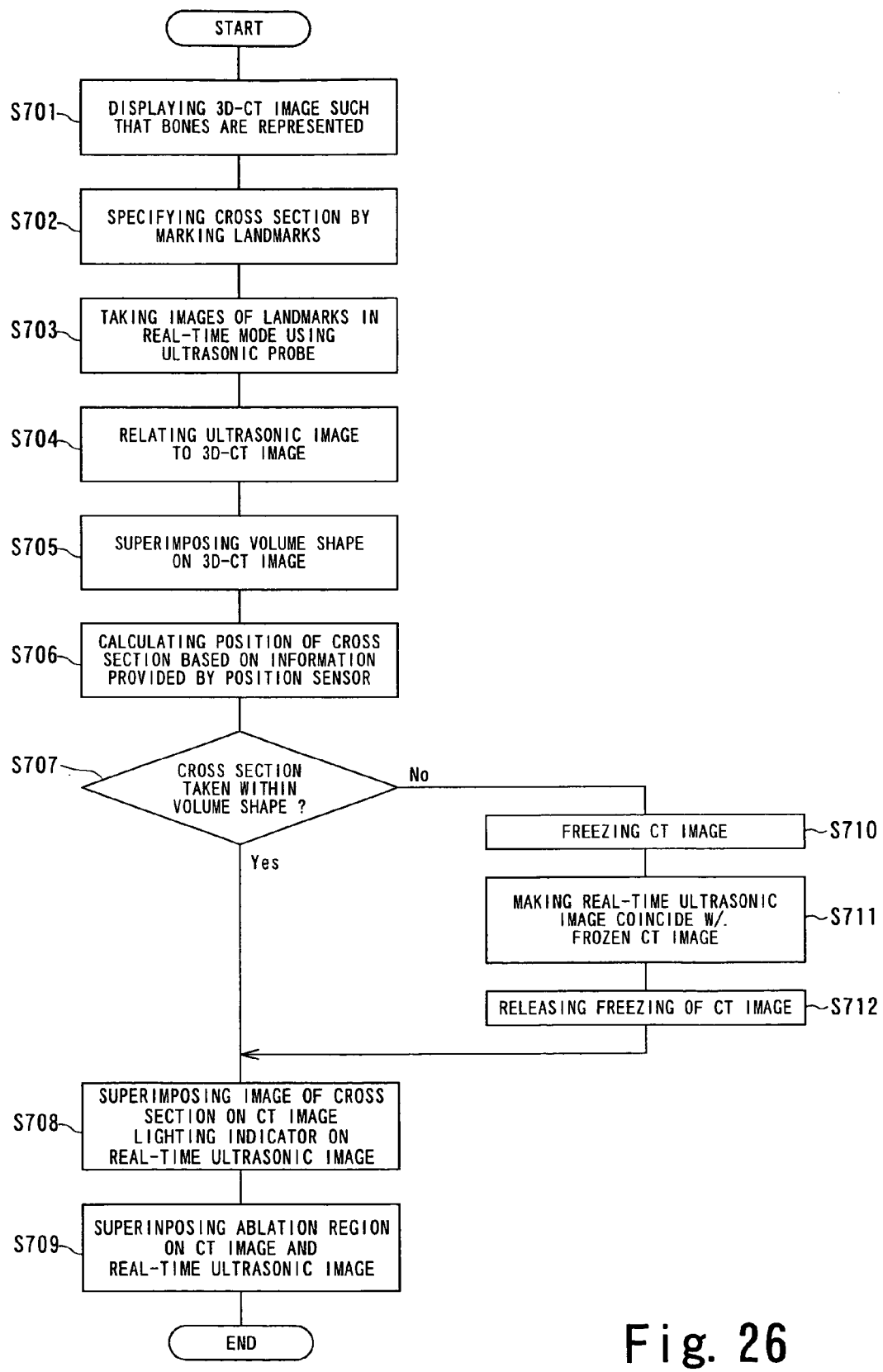
FIG. 26 is a flow chart showing an operation of the image processing/displaying apparatus according to the sixth embodiment of the present invention.

In the present embodiment, by way of example, it is assumed that the ultrasonic-imaging diagnostic system is used in paracentesis treatment of cancer of liver, and that 3-dimensional volume data is acquired using a CT scanner and a virtual ultrasonic image is displayed on the monitor 216. A typical work flow according to the present embodiment is described below with reference to a flow chart shown in FIG. 26.

Figure 27A:
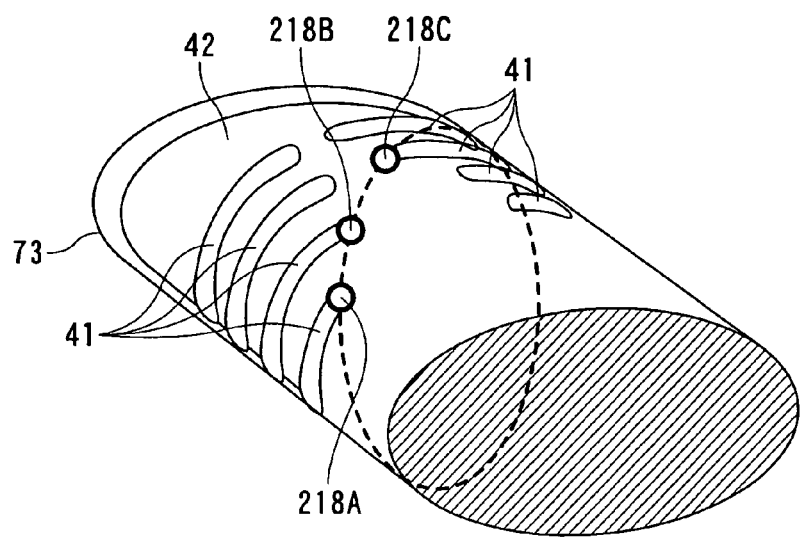
FIG. 27A is a diagram showing the concept of three points in a 3D-CT VR image.

First, as shown in FIG. 27A, a 3D-CT volume rendering image is displayed on the monitor 216 such that bones are represented (step S701). Three points of structures (such as an end of a costa) to be used as landmarks 218 whose ultrasonic image can be taken are marked using a pointing device such as a trackball (step S702) thereby specifying a cross section in a 3D-CT image space.

Figure 27B:
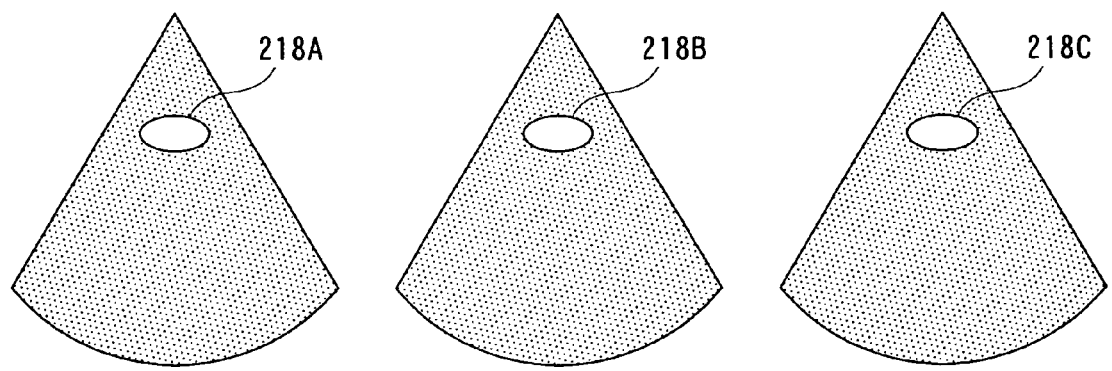
FIG. 27B is a diagram showing a manner of marking three points using an ultrasonic wave.

Thereafter, images of the landmarks 218 are taken in a normal real-time mode using the ultrasonic probe 212 with the position sensor (step S703). The three points corresponding to the landmarks are marked on the ultrasonic image thereby relating them to the landmarks on the CT image as shown in FIG. 27B (step S704). As a result of the marking, coordinates are related between the 3D-CT image space and the ultrasonic image space.

The marking of three points on the ultrasonic image may be performed such that 3-dimensional volume data is acquired by three-dimensionally scanning a region including the three points, an MPR image is displayed based on the 3-dimensional volume data, and three points are marked on the MPR image.

Figure 28:
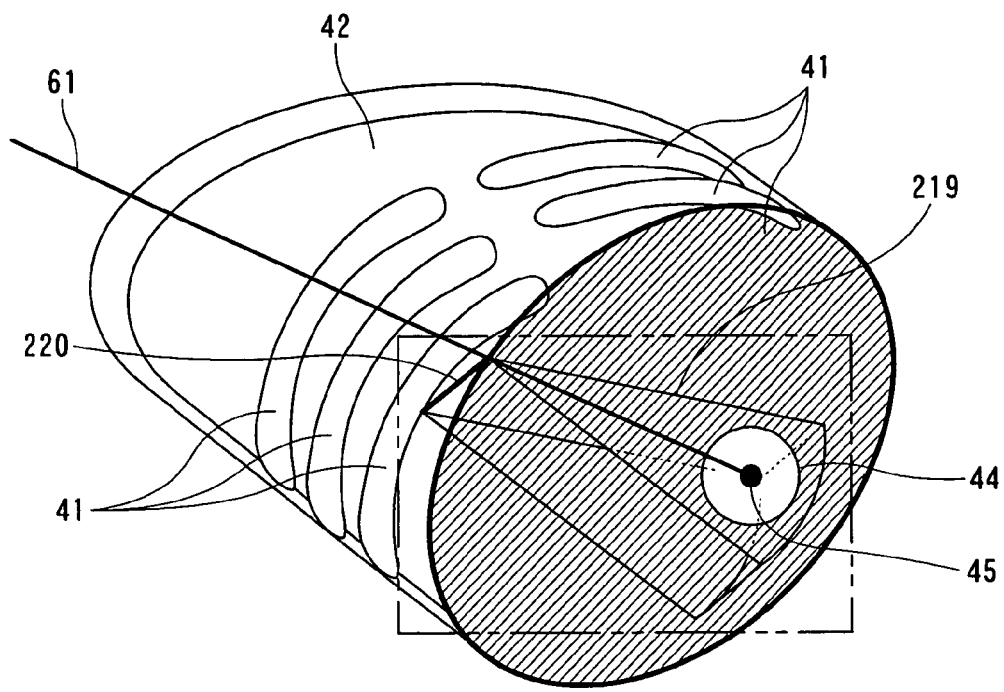
FIG. 28 is a diagram showing a manner in which a scanning volume shape is superimposed on a 3D-CT VR image.

In the case in which a mechanical 4D probe or a real-time 3D probe is used, a volume shape 219 scanned by the probe is superimposed on the CT image as shown in FIG. 28. In the other case, a volume shape 219 is calculated from the location, detected in planning of treatment, of the center of a tumor and from information associated with an ablation region, such that the volume shape circumscribes the ablation region, and the resultant volume shape 219 is superimposed on the CT image (step S705). In FIG. 28, the position of the volume scanned from the contact position 220 at which the ultrasonic probe 212 is in contact with the body surface is calculated from the probe position determined in the planning or from information which is provided by the position sensor 213 when the ultrasonic probe 212 is actually brought into contact with the body surface.

Figure 29:
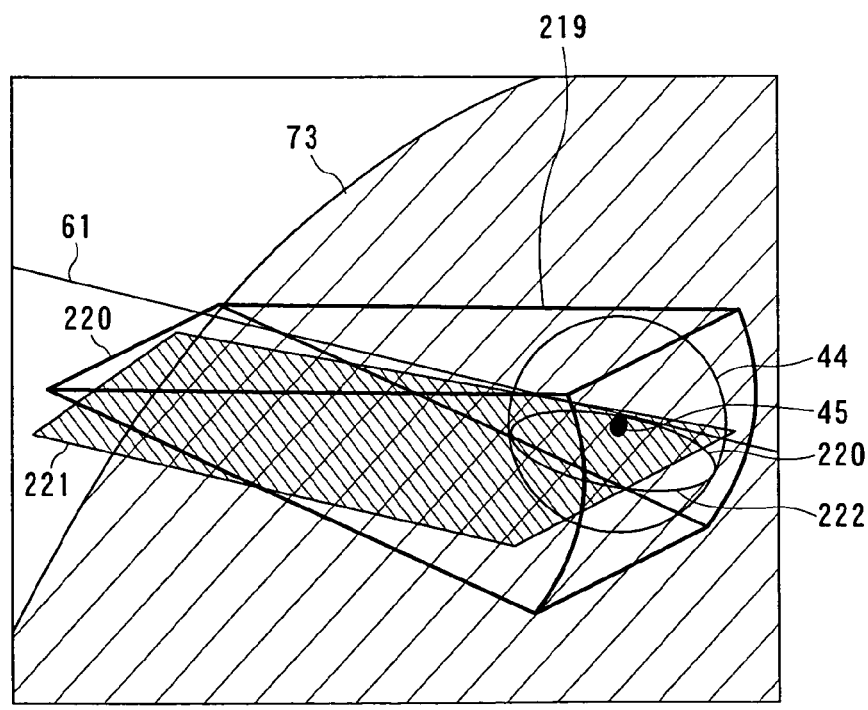
FIG. 29 is a diagram showing a manner of displaying, in a superimposed fashion, a position of a 2-dimensional imaging cross section calculated on the basis of information provided by a position sensor.

Thereafter the position of the 2-dimensional cross section 221 is calculated based on information provided by the position sensor so as to determine whether the 2-dimensional image of the cross section 221 being currently taken is within the 3D ultrasonic scanning volume shape 219 as shown in FIG. 29 (step S706). If the cross section 221 is within the 3D ultrasonic scanning volume shape 219 (that is, if the answer to step S707 is yes), the image of the cross section 221 is superimposed on the CT image (a) as shown in FIG. 29, and a circular-shaped blue indicator 223 is lit on the real-time ultrasonic image (b) to indicate that the cross section 221 is within the 3D ultrasonic scanning volume shape 219 (step S708).

Figure 30:
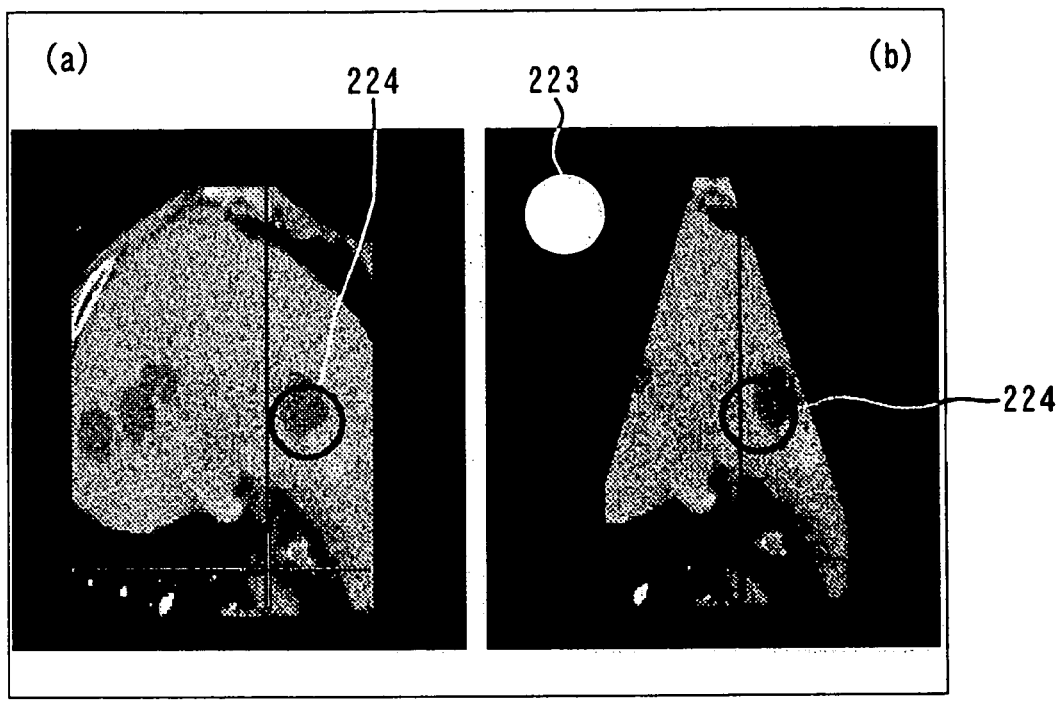
FIG. 30 is a diagram showing an example of a manner of displaying a CT cross section image and a real-time ultrasonic image side by side on the same screen.

In the case in which the image of the cross section 221 being currently taken is within the 3D ultrasonic scanning volume shape 219, the ablation region 224 determined in the planning is superimposed on the CT image (a) and the real-time ultrasonic image (b) as shown in FIG. 30 (step S709).

In the case in which the CT-image cross section and the real-time ultrasonic image are not sufficiently coincident with each other (that is, if the answer to step S707 is no), the CT-image cross section is frozen at a proper time and the real-time ultrasonic image is adjusted so as to coincide with the frozen CT-image cross section. After sufficient coincidence is achieved, the freezing is released so that the images are synchronously displayed again. As a result, errors in coordinates between the two image spaces are corrected (steps S710 to S712).

After finally determining the virtual ultrasonic cross section in the above-described manner, an ROI indicating a region of an ultrasonic cross section depending on the type of the ultrasonic probe used in treatment may be displayed in a superimposed manner.

In the present embodiment, it is possible to easily identify a tumor at a time immediately starting treatment or during the treatment, from information obtained based on the 3D modality image acquired in advance for use in paracentesis treatment using the ultrasonic diagnostic apparatus. This makes it possible to identify even a tumor of a type that cannot be easily identified by a conventional ultrasonic imaging technique. Besides, it is also possible to identify a plurality of tumors. Thus, it becomes possible to perform paracentesis treatment in a short time and in a highly reliable fashion.

Figure 31:
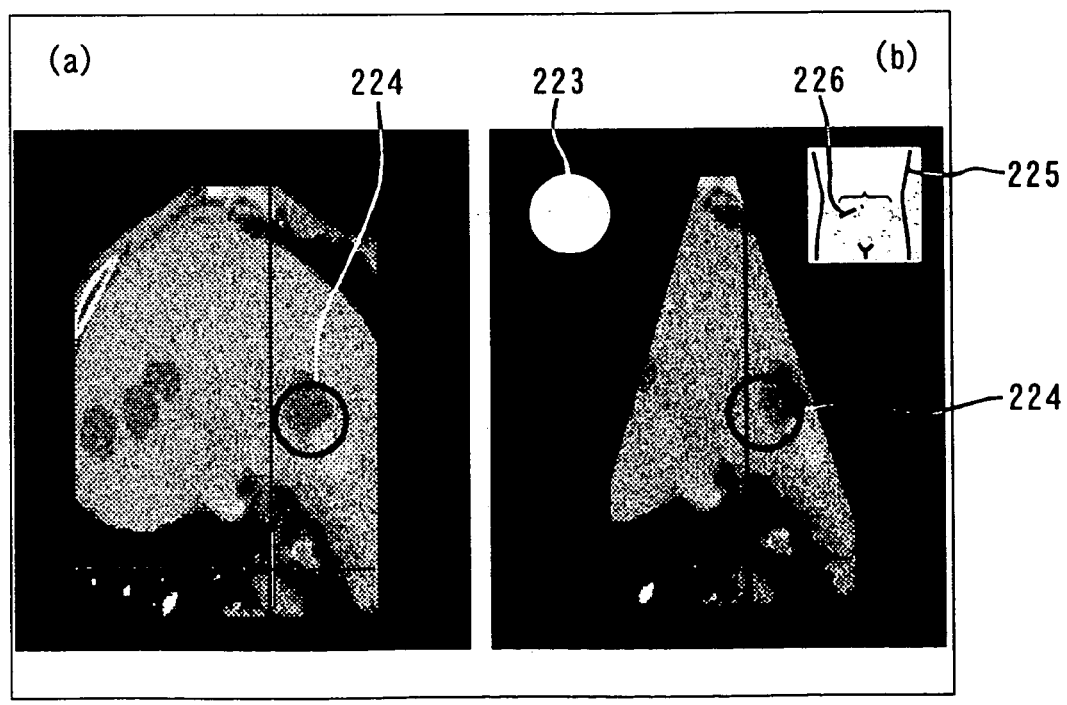
FIG. 31 is a diagram showing an example of a manner of displaying a body mark with a probe mark on the image shown in FIG. 30.

In an alternative embodiment, as shown in FIG. 31, to indicate the position of the ultrasonic probe on the subject, a body mark 225 with a probe mark 226 is displayed based on information provided by the position sensor, thereby making it possible for a user to easily recognize what position on subject is being currently scanned the ultrasonic image scanner and displayed.

Figure 32:
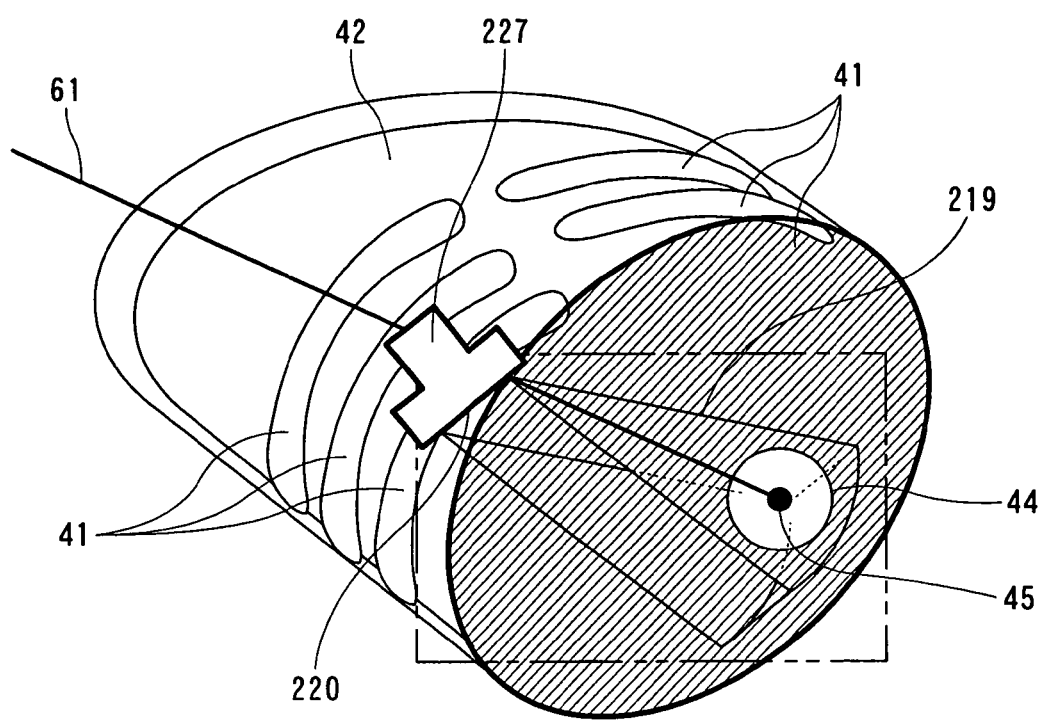
FIG. 32 is a diagram showing an example of a manner of displaying a graphical image of a ultrasonic probe superimposed on a body surface image.

A graphical image 227 of ultrasonic probe, such as a figure or a picture, may be superimposed on the body surface image acquired by means of surface rendering and displayed on the monitor 216 alternatively as shown in FIG. 32.

In this case, the main part 211 of the ultrasonic diagnostic apparatus comprises probe graphic storage unit for storing graphical image indicating the ultrasonic probe and body surface image generation unit for generating body surface image of the subject by means of surface rendering from the 3-dimensional volume data in 3-dimensional image generator 23 as described in the fifth embodiment. The graphical image 227 of ultrasonic probe generated by the body surface image generation unit displayed on the contact position 220 at which the ultrasonic probe 212 is in contact with the body surface calculated from the information which is provided by the position sensor 213 in a superimposed fashion.

The graphic image 227 of ultrasonic probe is displayed in a position of body surface suitable for acquiring a plane cut 43 which is displayed on 3-dimensional image display 24, for example, in a position indicated by the CPU to the probe position identification unit 26. The probe graphic storage unit may store a plurality of angles of graphical images so that an angle of graphical image adopted is changed over depending on the specified body surface, or may store a plurality of graphical images so that an adopted graphical image is changed over depending on a kind of ultrasonic probe registered or selected. Alternatively, the probe graphic storage unit may store not a plurality of graphical images but only a representative graphical image of ultrasonic probe.

Figure 33:
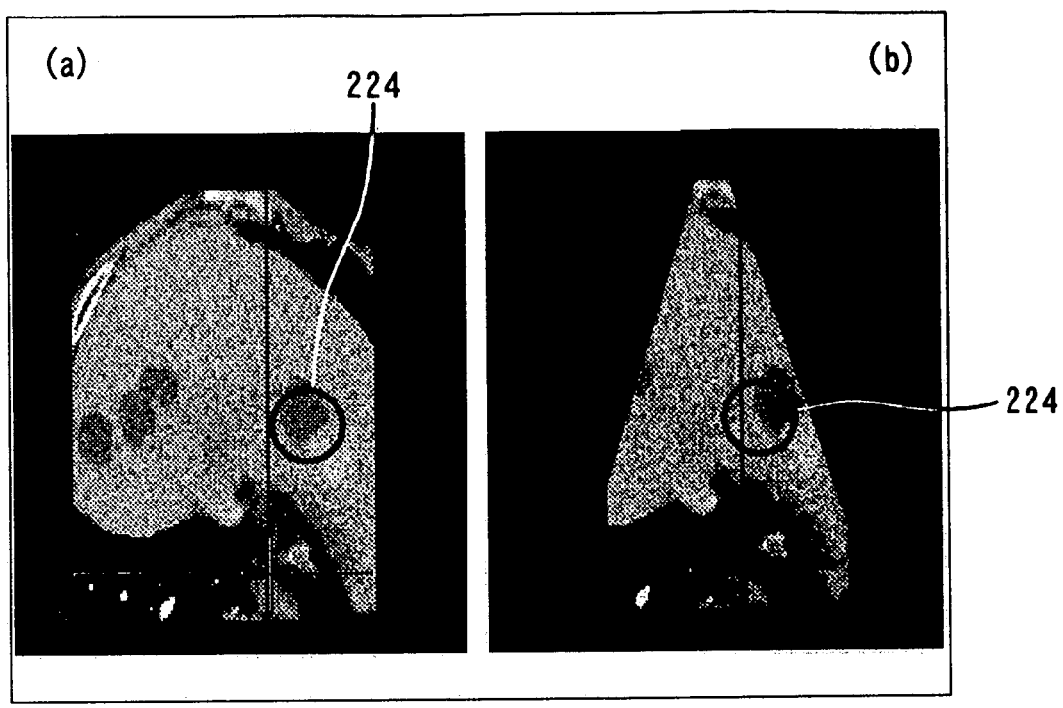
FIG. 33 is a diagram showing another example of a manner of displaying a CT cross section image and a real-time ultrasonic image side by side on the same screen.

In another alternative embodiment, relating of coordinates between the CT image space and the ultrasonic image space in steps S701 to S704 is not performed, but, as shown in a subscreen (a) in FIG. 33, a cross section acquired in the planning of treatment and a predicted volume shape such as that shown in FIG. 28 are displayed. At this stage, the cross section acquired in the planning of treatment is displayed in the form of a still image without being linked to information provided by the position sensor.

When the real-time ultrasonic image displayed in the subscreen (b) shown in FIG. 30 becomes coincident or nearly coincident with the cross section acquired in the planning of treatment and displayed in the subscreen (a) shown in FIG. 33, images (a) and (b) are linked, and the image of the planned ablation region is superimposed on the real-time ultrasonic image displayed in the subscreen (b) shown in FIG. 33.

This method makes it easy to perform relating of coordinates between the CT image space and the ultrasonic image space.

Although the present invention has been described above with reference to specific embodiments by way of example, the present invention is not limited to the details of those embodiments. It should be apparent to those skilled in the art that various modifications are possible by replacing some or all of elements with equivalent elements without departing from the spirit and scope of the present invention. The image processing/displaying apparatus and a method of controlling the same is applied in the planning of paracentesis or in the actual paracentesis treatment in the embodiments above, however, it may be applied after actual paracentesis in order to easily make comparison among images acquired by different kinds of modality with each other, for example.

What is claimed is:

1. An image processing/displaying apparatus comprising:
a data storage unit configured to store 3-dimensional volume data;
a cross section information generation unit configured to generate cross section information by reconstructing the 3-dimensional volume data stored in the data storage unit;
an image display unit configured to display a cross section image of a subject in accordance with the cross section information generated by the cross section information generation unit;
a free moving control unit configured to control moving of a plane cut through the subject as a free-moving stage to locate a plane cut passing through an affected part of the subject;
a lock instruction unit configured to generate a lock instruction to lock the plane cut;
a locking unit configured to receive the lock instruction of the lock instruction unit and allow locking of the plane cut passing through the affected part of the subject;
a rotating center setting unit configured to set a rotating center on the affected part in the plane cut locked by the locking unit;
a limited moving control unit configured to allow rotational moving of the locked plane cut around the rotating center set by the rotating center setting unit and to disable parallel moving of the locked plane cut as a limited-moving stage after the free-moving stage; and
a needle insertion path setting unit configured to set a paracentesis needle insertion path such that when an insertion point at which to insert a paracentesis needle is specified on a plane cut taken in the cross section image including the affected part or in the cross section image displayed together with the plane cut, a straight line is drawn between the specified insertion point and the affected part thereby setting the paracentesis needle insertion path,
wherein the image display unit displays the paracentesis needle insertion path and a region of a virtual paracentesis ultrasonic cross section of the image of the subject in a superimposed fashion, and a scan region depending on a type of an ultrasonic probe.

2. The image processing/displaying apparatus according to claim 1, wherein when a paracentesis needle insertion path is set by the needle insertion path setting unit, the image display unit displays images of two orthogonal cross sections orthogonally intersecting along the paracentesis needle insertion path with each other and a cross section image perpendicular to the paracentesis needle insertion path such that the cross sections are in positions moved by predetermined distances within a predetermined range along the paracentesis needle insertion path.

3. The image processing/displaying apparatus according to claim 2, wherein
the image display unit displays a 3-dimensional image generated by means of volume rendering; and
the needle insertion path setting unit specifies a paracentesis needle insertion point on the basis of the 3-dimensional image.

4. The image processing/displaying apparatus according to claim 2, wherein
the image display unit displays an arbitrary cross section and an MPR image of three orthogonal cross sections; and
the needle insertion path setting unit specifies a paracentesis needle insertion point on the basis of the arbitrary cross section and the MPR image of the three orthogonal cross sections.

5. The image processing/displaying apparatus according to claim 2, wherein the image display unit displays an image of a first cross section including a paracentesis needle insertion path set by the needle insertion path setting unit, an image of a second cross section including the paracentesis needle insertion path and perpendicular to the first cross section, an image of a third cross section perpendicular to the paracentesis needle insertion path, and a 3-dimensional image generated by means of volume rendering.

6. The image processing/displaying apparatus according to claim 2, wherein the image display unit displays a composite image of a 3-dimensional image including a paracentesis needle insertion path generated by means of volume rendering and a virtual ultrasonic cross section image, and also displays a live image taken by an ultrasonic diagnostic apparatus.

7. The image processing/displaying apparatus according to claim 2, wherein the needle insertion path setting unit is capable of changing the specified insertion point of the paracentesis needle when some of the cross section images includes a part that should be avoided from the paracentesis needle insertion path.

8. The image processing/displaying apparatus according to claim 1, wherein the data storage unit acquires 3-dimensional volume data from one or more of an X-ray 3-dimensional imaging apparatus, an X-ray CT scanner, an MRI scanner, an ultrasonic diagnostic apparatus, and a nucleus medical diagnostic apparatus.

9. A method of controlling an image processing/displaying apparatus comprising:
a first step of displaying a cross section image of a subject in accordance with 3-dimensional volume data indicating information of the subject;

a second step of controlling moving of a plane cut through the subject as a free-moving stage to locate a plane cut through an affected part of the subject;

a third step of generating a lock instruction to lock the plane cut;

a fourth step of receiving the lock instruction and allow locking of the plane cut through the affected part of the subject;

a fifth step of setting a rotating center on the affected part in the plane cut locked in the fourth step;

a sixth step of allowing rotational moving of the locked plane cut around the rotating center set in the fifth step, and disabling parallel moving of the locked plane cut as a limited-moving stage after the free-moving stage, and displaying a rotated image;

a seventh step of specifying a point on the rotated image displayed in the sixth step thereby setting a paracentesis needle insertion path;

an eighth step of setting a paracentesis needle insertion path by drawing a straight line between the point and the affected part; and a ninth step of displaying the paracentesis needle insertion path and a region of a virtual paracentesis ultrasonic cross section image of the subject in a superimposed fashion, and a scan region depending on a type of an ultrasonic probe.

10. The image processing/displaying apparatus according to claim 2, further comprising a body surface image generation unit configured to generate a body surface image of the subject by means of surface rendering from the 3-dimensional volume data stored in the data storage unit; and the image display unit displays the body surface image generated by the body surface image generation unit so as to be superimposed on a 3-dimensional image.

11. The image processing/displaying apparatus according to claim 10, further comprising a graphic data generation unit configured to generate graphic data indicating the position of a virtual ultrasonic cross section and graphic data indicating a paracentesis needle from the 3-dimensional volume data stored in the data storage unit; and the image display unit displays a graphic image based on the graphic data generated by the graphic data generation unit so as to be superimposed on the 3-dimensional image.

12. The image processing/displaying apparatus according to claim 2, further comprising a graphic data generation unit configured to generate graphic data indicating the position of a virtual ultrasonic cross section and graphic data indicating a paracentesis needle from the 3-dimensional volume data stored in the data storage unit; and the image display unit displays a graphic image based on the graphic data generated by the graphic data generation unit so as to be superimposed on the 3-dimensional image.

13. The image processing/displaying apparatus according to claim 12, wherein the image display unit displays the graphic image superimposed on the 3-dimensional image such that the graphic image is erasable.

14. The image processing/displaying apparatus according to claim 10, wherein the image display unit displays a mark on a surface of the subject so as to be superimposed on the 3-dimensional image.

15. The image processing/displaying apparatus according to claim 10, wherein the image display unit displays a center line of the subject so as to be superimposed on the 3-dimensional image.

16. The image processing/displaying apparatus according to claim 10, further comprising a probe graphic storage unit configured to store a graphical image representing a paracentesis probe and a physical relationship between the paracentesis probe and a paracentesis needle, wherein the image display unit displays the graphical image representing a paracentesis probe at the location where the paracentesis probe touches a body surface of the body surface image and where the plane cut intersects the body surface so as to be superimposed on the body surface image generated by the body surface image generating unit.

17. The method of controlling an image processing/displaying apparatus according to claim 9, comprising displaying, in the same screen, an ultrasonic image of the subject with the paracentesis needle and said virtual ultrasonic paracentesis cross section.

18. The image processing/displaying apparatus according to claim 1, wherein the image display unit displays, in the same screen, an ultrasonic image of the subject with the paracentesis needle and said virtual ultrasonic paracentesis cross section.

* * * * *